(12) United States Patent
Min et al.

(10) Patent No.: US 8,170,687 B2
(45) Date of Patent: May 1, 2012

(54) IMPLANTABLE MEDICAL DEVICE LEAD INCORPORATING INSULATED COILS FORMED AS INDUCTIVE BANDSTOP FILTERS TO REDUCE LEAD HEATING DURING MRI

(75) Inventors: Xiaoyi Min, Thousand Oaks, CA (US); Peter A. Nichols, Canyon County, CA (US)

(73) Assignee: Pacesetter, Inc., Sylmar, CA (US)

( * ) Notice: Subject to any disclaimer, the term of this patent is extended or adjusted under 35 U.S.C. 154(b) by 65 days.

(21) Appl. No.: 12/537,880

(22) Filed: Aug. 7, 2009

(65) Prior Publication Data

US 2011/0034979 A1 Feb. 10, 2011

(51) Int. Cl.
*A61N 1/00* (2006.01)
(52) U.S. Cl. ....................................................... 607/116
(58) Field of Classification Search .................. 607/116, 607/119
See application file for complete search history.

(56) References Cited

U.S. PATENT DOCUMENTS

| | | | |
|---|---|---|---|
| 4,746,864 A | 5/1988 | Satoh | |
| 5,063,348 A | 11/1991 | Kuhara et al. | |
| 6,871,091 B2 | 3/2005 | Wilkinson et al. | |
| 6,930,242 B1 | 8/2005 | Helfer et al. | |
| 6,944,489 B2 | 9/2005 | Zeijlemaker et al. | |
| 7,015,393 B2 | 3/2006 | Weiner et al. | |
| 7,091,412 B2 | 8/2006 | Wang et al. | |
| 7,127,294 B1 | 10/2006 | Wang et al. | |
| 7,162,302 B2 | 1/2007 | Wang et al. | |
| 7,529,590 B2 | 5/2009 | MacDonald | |
| 2003/0144718 A1 | 7/2003 | Zeijlemaker | |
| 2003/0144719 A1 | 7/2003 | Zeijlemaker | |
| 2004/0210289 A1 | 10/2004 | Wang et al. | |
| 2004/0230271 A1 | 11/2004 | Wang et al. | |
| 2004/0249428 A1 | 12/2004 | Wang et al. | |
| 2005/0113669 A1 | 5/2005 | Helfer et al. | |
| 2005/0113676 A1 | 5/2005 | Weiner et al. | |
| 2005/0113873 A1 | 5/2005 | Weiner et al. | |
| 2005/0113874 A1 | 5/2005 | Connelly et al. | |
| 2005/0113876 A1 | 5/2005 | Weiner et al. | |
| 2005/0222658 A1 | 10/2005 | Hoegh et al. | |
| 2005/0222659 A1 | 10/2005 | Olsen et al. | |
| 2005/0247472 A1 | 11/2005 | Helfer et al. | |
| 2006/0119361 A1 | 6/2006 | Karmarkar et al. | |
| 2006/0200218 A1 | 9/2006 | Wahlstrand | |
| 2006/0271138 A1 | 11/2006 | MacDonald | |

(Continued)

FOREIGN PATENT DOCUMENTS

WO 03063952 A2 8/2003

(Continued)

*Primary Examiner* — George Manuel
*Assistant Examiner* — Robert Wieland

(57) ABSTRACT

To provide radio-frequency (RF) bandstop filtering within an implantable lead, such as a pacemaker lead, one or more segments of the tip and ring conductors of the lead are formed as insulated coils to function as inductive band stop filters. By forming segments of the conductors into insulated coils, a separate set of discrete or distributed inductors is not required, yet RF filtering is achieved to, e.g., reduce lead heating during magnetic resonance imaging (MRI) procedures. To enhance the degree of bandstop filtering at the RF signal frequencies of MRIs, additional capacitive elements are added. In one example, the ring electrode of the lead is configured to provide capacitive shunting to the tip conductor. In another example, a capacitive transition is provided between the outer insulated coil and proximal portions of the ring conductor. In still other examples, conducting polymers are provided to enhance capacitive shunting. The insulated coils may be spaced at ¼ wavelength locations.

32 Claims, 17 Drawing Sheets

U.S. PATENT DOCUMENTS

| | | | |
|---|---|---|---|
| 2007/0185556 A1* | 8/2007 | Williams et al. | 607/116 |
| 2007/0299490 A1 | 12/2007 | Yang et al. | |
| 2008/0004670 A1 | 1/2008 | McVenes et al. | |
| 2008/0033497 A1 | 2/2008 | Bulkes et al. | |
| 2008/0039709 A1 | 2/2008 | Karmarkar | |
| 2008/0132986 A1 | 6/2008 | Gray et al. | |
| 2008/0195186 A1 | 8/2008 | Li et al. | |
| 2008/0195187 A1 | 8/2008 | Li et al. | |
| 2008/0243218 A1 | 10/2008 | Bottomley et al. | |
| 2008/0262584 A1* | 10/2008 | Bottomley et al. | 607/119 |
| 2009/0099555 A1 | 4/2009 | Viohl et al. | |
| 2011/0029054 A1* | 2/2011 | Tranchina | 607/116 |

FOREIGN PATENT DOCUMENTS

| | | |
|---|---|---|
| WO | 03063952 A3 | 8/2003 |
| WO | 2005081784 A2 | 9/2005 |
| WO | 2005081784 A3 | 9/2005 |
| WO | 2005115531 A2 | 12/2005 |
| WO | 2005115531 A3 | 12/2005 |
| WO | 2006093685 A1 | 9/2006 |
| WO | 2007047966 A2 | 4/2007 |
| WO | 2007047966 A3 | 4/2007 |
| WO | 2008111986 A1 | 9/2008 |

* cited by examiner $I1 = Y11 \times V1 + Y12 \times V2 + Y13 \times V3 + Y14 \times V4$ $I2 = Y21 \times V1 + Y22 \times V2 + Y23 \times V3 + Y24 \times V4$ $I3 = Y31 \times V1 + Y32 \times V2 + Y33 \times V3 + Y34 \times V4$ $I4 = Y41 \times V1 + Y42 \times V2 + Y43 \times V3 + Y44 \times V4$

IMPLANTABLE MEDICAL DEVICE LEAD INCORPORATING INSULATED COILS FORMED AS INDUCTIVE BANDSTOP FILTERS TO REDUCE LEAD HEATING DURING MRI

CROSS-REFERENCE TO RELATED APPLICATIONS

This application is related to U.S. Patent Application Publication No. 2011/0034983-A1, filed concurrently herewith, titled "Implantable Medical Device Lead Incorporating a Conductive Sheath Surrounding Insulated Coils to Reduce Lead Heating During MRI", which is currently pending and incorporated by reference herein in its entirety.

FIELD OF THE INVENTION

The invention generally relates to leads for use with implantable medical devices, such as pacemakers or implantable cardioverter-defibrillators (ICDs) and, in particular, to components for use within such leads to reduce heating during magnetic resonance imaging (MRI) procedures.

BACKGROUND OF THE INVENTION

MRI is an effective, non-invasive magnetic imaging technique for generating sharp images of the internal anatomy of the human body, which provides an efficient means for diagnosing disorders such as neurological and cardiac abnormalities and for spotting tumors and the like. Briefly, the patient is placed within the center of a large superconducting magnet that generates a powerful static magnetic field. The static magnetic field causes protons within tissues of the body to align with an axis of the static field. A pulsed RF magnetic field is then applied causing the protons to begin to precess around the axis of the static field. Pulsed gradient magnetic fields are then applied to cause the protons within selected locations of the body to emit RF signals, which are detected by sensors of the MRI system. Based on the RF signals emitted by the protons, the MRI system then generates a precise image of the selected locations of the body, typically image slices of organs of interest.

However, MRI procedures are problematic for patients with implantable medical devices such as pacemakers and ICDs. One of the significant problems or risks is that the strong RF fields of the MRI can induce currents through the lead system of the implantable device into the tissues, resulting in Joule heating in the cardiac tissues around the electrodes of leads and potentially damaging adjacent tissues. Indeed, the temperature at the tip or ring of an implanted lead has been found to increase as much as 60° for tip or 20° for ring Celsius (C.) during an MRI tested in a gel phantom in a non-clinical configuration. Although such a dramatic increase is probably unlikely within a clinical system wherein leads are properly implanted, even a temperature increase of only about 8°-13° C. might cause myocardial tissue damage.

Furthermore, any significant heating of cardiac tissues near lead electrodes can affect the pacing and sensing parameters associated with the tissues near the electrode, thus potentially preventing pacing pulses from being properly captured within the heart of the patient and/or preventing intrinsic electrical events from being properly sensed by the device. The latter might result, depending upon the circumstances, in therapy being improperly delivered or improperly withheld. Another significant concern is that any currents induced in the lead system can potentially generate voltages within cardiac tissue comparable in amplitude and duration to stimulation pulses and hence might trigger unwanted contractions of heart tissue. The rate of such contractions can be extremely high, posing significant clinical risks to patients. Therefore, there is a need to reduce heating in the leads of implantable medical devices, especially pacemakers and ICDs, and to also reduce the risks of improper tissue stimulation during an MRI, which is referred to herein as MRI-induced pacing.

Various techniques have been developed to address these or other related concerns. See, for example, the following patents and patent applications: U.S. patent application Ser. No. 11/943,499, filed Nov. 20, 2007, of Zhao et al., entitled "RF Filter Packaging for Coaxial Implantable Medical Device Lead to Reduce Lead Heating during MRI"; U.S. patent application Ser. No. 12/117,069, filed May 8, 2008, of Vase, entitled "Shaft-mounted RF Filtering Elements for Implantable Medical Device Lead to Reduce Lead Heating During MRI"; U.S. patent application Ser. No. 11/860,342, filed Sep. 27, 2007, of Min et al., entitled "Systems and Methods for using Capacitive Elements to Reduce Heating within Implantable Medical Device Leads during an MRI"; U.S. patent application Ser. No. 12/042,605, filed Mar. 5, 2009, of Mouchawar et al., entitled "Systems and Methods for using Resistive Elements and Switching Systems to Reduce Heating within Implantable Medical Device Leads during an MRI"; and U.S. patent application Ser. 11/963,243, filed Dec. 21, 2007, of Vase et al., entitled "MEMS-based RF Filtering Devices for Implantable Medical Device Leads to Reduce Lead Heating during MRI."

See, also, U.S. patent application Ser. No. 12/257,263, filed Oct. 23, 2008, of Min, entitled "Systems and Methods for Exploiting the Tip or Ring Conductor of an Implantable Medical Device Lead during an MRI to Reduce Lead Heating and the Risks of MRI-Induced Stimulation; U.S. patent application Ser. No. 12/257,245, filed Oct. 23, 2008, of Min, entitled "Systems and Methods for Disconnecting Electrodes of Leads of Implantable Medical Devices during an MRI to Reduce Lead Heating while also providing RF Shielding"; and U.S. patent application Ser. No. 12/270,768, of Min et al., filed Nov. 13, 2008, entitled "Systems And Methods For Reducing RF Power or Adjusting Flip Angles During an MRI For Patients with Implantable Medical Devices."

At least some of these techniques are directed to installing RF filters, such as inductive (L) filters or inductive-capacitive (LC) filters, within the leads for use in filtering signals at frequencies associated with the RF fields of MRIs. It is particularly desirable to select or control of the inductance (L), parasitic capacitance (Cs) and parasitic resistance (Rs) of such devices to attain a high target impedance (e.g. at least 1000 ohms) at RF to achieve effective heat reduction. See, for example, U.S. patent application Ser. No. 11/955,268, filed Dec. 12, 2007, of Min, entitled "Systems and Methods for Determining Inductance and Capacitance Values for use with LC Filters within Implantable Medical Device Leads to Reduce Lead Heating During an MRI; and U.S. patent application Ser. No. 12/325,945, of Min et al., filed Dec. 1, 2008, entitled "Systems and Methods for Selecting Components for Use in RF Filters within Implantable Medical Device Leads based on Inductance, Parasitic Capacitance and Parasitic Resistance."

Although these techniques are helpful in reducing lead heating due to MRI fields, there is room for further improvement. In particular, it would be desirable to provide RF filtering without requiring one or more discrete or lumped L or LC filters, as such filters can be harder to be implemented in a limited space allowed in a lead and to meet required mechanical reliability. One possible solution is to provide for some form of distributed inductance along the length of the lead. However, problems arise in providing distributed inductance along medical device leads, particularly the leads of pacemakers and ICDs.

One such problem is due to the "coiling effect." It has been found that any coiling of excess lead length by the clinician during device implant can affect the amount of heat reduction achieved using distributed RF filtering elements. In this regard, following implant of the distal ends of leads into heart chambers, and prior to connection of the proximal ends of the leads into the pacemaker or ICD being implanted, there may be some excess lead length. Clinicians often wrap or coil the excess lead length around or under the pacemaker or ICD prior to connecting the leads to the device. This can negate the efficacy of heat reduction features in leads, particularly the efficacy of distributed inductive filtering components, potentially resulting in an increase of over 30° C. as compared to leads not coiled around or under the device. This interference in heat reduction caused by wrapping the lead around or under the device is referred to herein as the coiling effect.

It is believed that the coiling effect may be due to shunt capacitance between the proximal portions of the lead that are wrapped around or under the device and the housing of the device itself (particularly when proximal portions of the leads include some form of inductive filtering element) as well as changes related to loops (such as impedance/phase changes at the location of the end of coiling section.) As noted, a high target impedance at RF is desired to reduce heating due to the RF fields of the MRI. Insofar as leads with distributed inductive components are concerned, the actual impedance achieved depends, in part, on the inductance (L) and the parasitic capacitance and resistance (Cs, Rs) of the components distributed along the lead. Coiling the lead around or under a device appears to reduce the inductance of insulated coils and also add a shunt capacitance between the distributed components along the proximal end of the lead and the metallic case of the device, which adversely affects the resulting L, Cs and Rs values and hence allows for greater unwanted heating during MRIs when the performance depends on accumulated effect of distributed insulated coils.

So, one concern with implementing distributed inductive RF filters within leads is shunt capacitance due to the coiling effect (particularly involving any distributed components mounted along the proximal end of the lead.). This can be related to lead length if the shortest possible lead length in clinical setting (e.g. 25 cm or shorter) does not meet impedance requirements for RF heating reduction.

Accordingly, it would be desirable to provide improved lead designs that achieve heat reduction during MRIs without requiring conventional discrete or lumped RF filtering components and without requiring otherwise conventional distributed filtering components. Various aspects of the invention are directed to this end.

SUMMARY OF THE INVENTION

In accordance with various exemplary embodiments of the invention, a lead is provided for use with an implantable medical device for implant within a patient wherein the lead includes: an electrode for placement adjacent patient tissues; and a conductor operative to route signals along the lead between the electrode and the implantable medical device, with a portion or segment of the conductor formed as an insulated coil and configured to provide inductive bandstop filtering element for filtering RF signals. By forming a portion of the conductor as an insulated coil to provide inductive bandstop filtering, a set of discrete or lumped L or LC components are not required, yet RF filtering can be achieved to reduce heat during MRIs. Moreover, unlike conventional distributed inductor designs (which typically extend along the entire lead length), the insulated coil portion of the conductor can be formed along only a relatively short portion of the lead (such as along only the distal end of the lead.) This helps avoid problems arising due to the coiling effect.

In an illustrative embodiment, wherein the lead is for use with a pacemaker or ICD, the lead is a co-axial bipolar lead. The lead has an inner tip conductor leading to a tip electrode at a distal end of the lead and also has an outer ring conductor leading to a ring electrode at the distal end of the lead. Distal portions of both the tip and ring conductors are formed as insulated coils (of up to 10 cm in length) to provide for inductive bandstop filtering of RF signals. Preferably, the inner coil is nested within the outer coil. In one particular example, the insulated nested coils are each 5 cm in length and have about 400 turns with a self-resonance frequency (SRF) of about 100 MHz. Optimization of lead parameters may then be performed to achieve adequate impedance at, at least some, RF signal frequencies so as to achieve a significant degree of RF bandstop filtering.

In some examples of the coaxial lead, capacitive devices are also provided along with the inductive coils of the tip and ring conductors so as to provide LC filtering. In one particular example, the ring electrode is configured and positioned relative to the tip conductor to provide a capacitance therebetween. For example, the ring electrode can be configured to have a relatively narrow inner diameter and a relatively long length to provide the capacitance. In still other examples, a capacitive transition is provided between the ring inductive coil and other portions of the ring conductor. The capacitive transition is preferably configured so as to achieve a certain voltage or current relationship between the tip and ring conductors.

Additionally or alternatively, a shielding layer made of metallic layer/meshes or conducting polymers can be placed over the insulated coils or can be embedded inside insulation tubing or exposed to fluid.

Within coaxial examples, a conducting polymer tubing may be provided along the lead between the ring electrode and the insulated coil portion of the inner (tip) conductor so as to provide an RF short or decoupler. A conducting polymer core may be provided within the inner insulated coil, as well. In some examples, each conductor of the coaxial lead includes two or more portions or segments formed as insulated coils. A conducting polymer may be provided between the two segments. The two segments may also be configured to provide different SRFs to as to achieve bandstop filtering at different RF signal frequencies, preferably at about 64 MHz and at about 128 MHz. (It should be understood that 64 MHz and 128 MHz are merely approximate values for the MRI frequencies. More precisely, MRIs typically operate at 63.7±0.345 MHz with 1.5 T and 125.6±3.6 MHz with 3.0 T.)

Band stop filters formed by insulated coils can also be located at both distal and proximal ends of coils in the lead. For coaxial leads, it is preferred for the filters to be provided on the outer coils because it is easier to form a band stop filter on an outer coil due to the larger outer coil diameters. Moreover, a band stop filter on the outer coil can achieve better suppression of induced currents via shielding.

The use of insulated coils along the conductors is particularly well-suited for use with bipolar coaxial cardiac pacing/sensing leads for use with pacemakers and ICDs but may also be employed in connection with other cardiac pacing/sensing leads, such as co-radial leads, or leads for use with other implantable medical devices.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. The description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of MRI System

Figure 1:
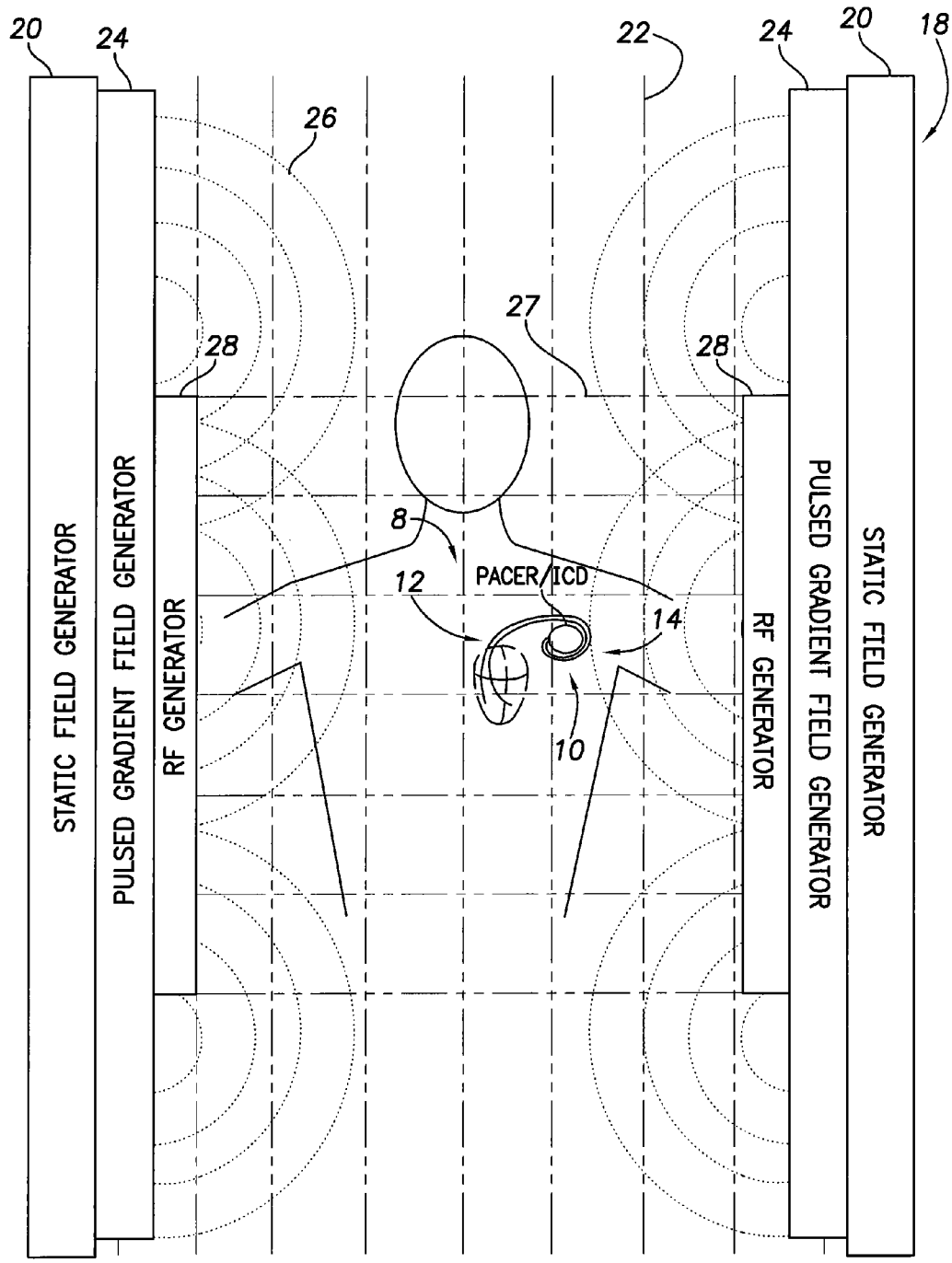
FIG. 1 is a stylized representation of an MRI system along with a patient with a pacer/ICD implanted therein with bipolar RV and LV leads employing internal insulated coils (not shown) near their distal ends and also illustrating the coiling of the proximal ends of the leads around the pacer/ICD.

FIG. 1 illustrates an implantable medical system 8 having a pacer/ICD 10 for use with a set of bipolar pacing/sensing leads 12. In the example, proximal portions 14 of the leads have been wrapped around the pacer/ICD, as can occur if the clinician chooses to wrap excess portions of the lead around or under the device during device implant. As explained, the coiling of the lead around or under the pacer/ICD by the clinician can adversely affect heat reduction achieved by RF filters within the lead (none of which are shown in FIG. 1.) As such, greater heating can occur within the lead and surrounding tissues due to the fields generated by an MRI system 18, than if the lead were not wrapped around the pacer/ICD. This is the coiling effect described above.

Figure 15:
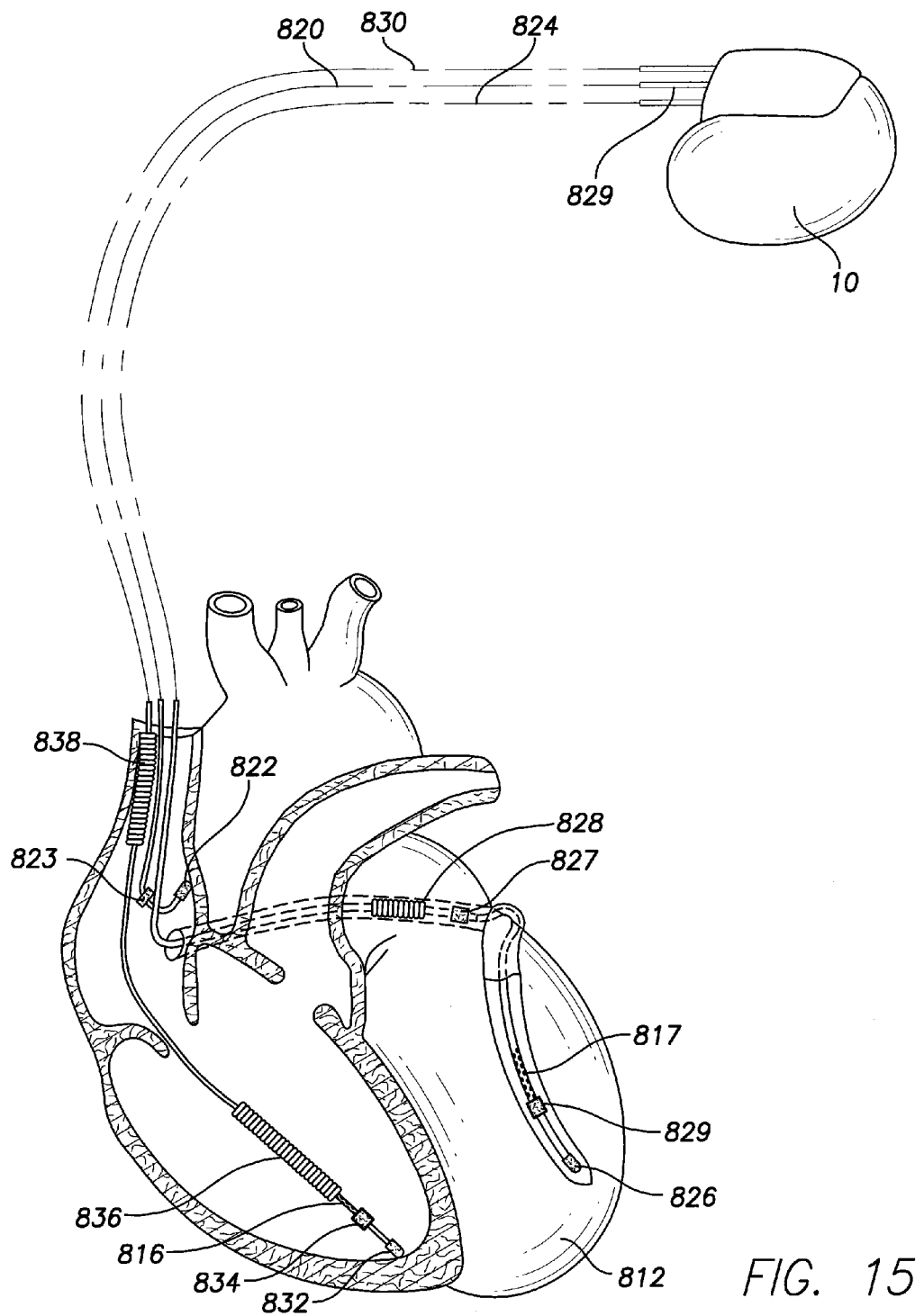
FIG. 15 is a simplified, partly cutaway view, illustrating the pacer/ICD of FIG. 1 (without any coiling of the leads around the device), along with a more complete set of leads implanted in the heart of the patient, wherein the RV and LV leads include insulated coil bandstop filtering devices near distal ends of the leads.
Figure 16:
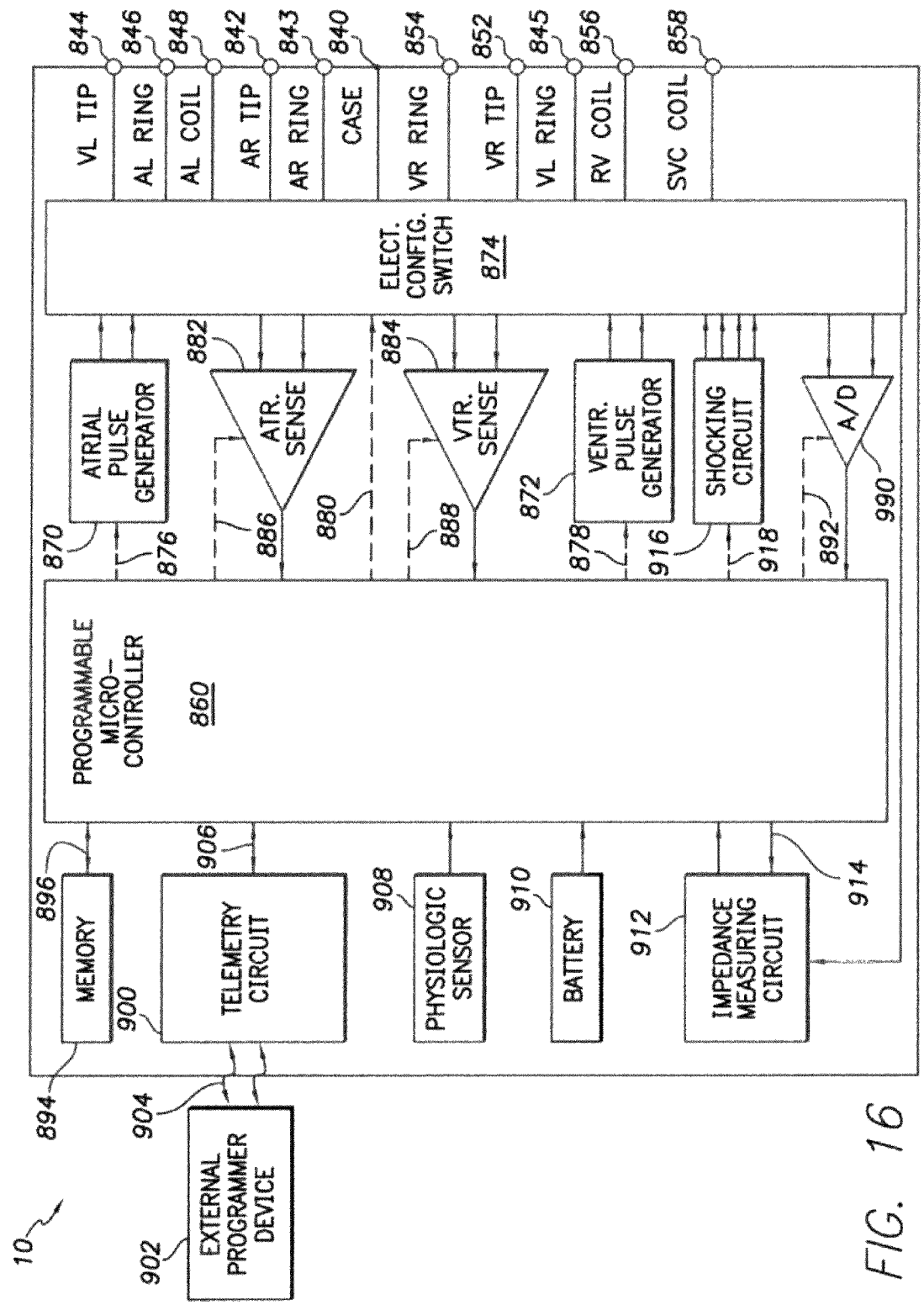
FIG. 16 is a functional block diagram of the pacer/ICD of FIG. 15, illustrating basic circuit elements that provide cardioversion, defibrillation and/or pacing stimulation in four chambers of the heart.

As will be explained in more detail below, leads 12 each include insulated coils to provide inductive RF bandpass filtering for MRI heat reduction while avoiding possible adverse coiling effects between the insulated coils of the leads and the conducting housing of pacer/ICD. In FIG.1, these insulated coils are not separately shown, as the coils are internal the lead. Note also that in FIG. 1 only two leads are shown, a right ventricular (RV) lead and a left ventricular (LV) lead. A more complete lead system is illustrated in FIG. 15, described below.

As to MRI system 18, the system includes a static field generator 20 for generating a static magnetic field 22 and a pulsed gradient field generator 24 for selectively generating pulsed gradient magnetic fields 26. The MRI system also includes an RF generator 28 for generating RF fields 27. Other components of the MRI, such as its sensing and imaging components are not shown. MRI systems and imaging techniques are well known and will not be described in detail herein. For exemplary MRI systems see, for example, U.S. Pat. No. 5,063,348 to Kuhara, et al., entitled "Magnetic Resonance Imaging System" and U.S. Pat. No. 4,746,864 to Satoh, entitled "Magnetic Resonance Imaging System." Note that the fields shown in FIG. 1 are stylized representations of MRI fields intended merely to illustrate the presence of the fields. Actual MRI fields generally have far more complex patterns.

Hence, the leads of pacer/ICD 10 include insulated coils therein for use in reducing lead heating during MRI procedures.

Exemplary Lead Implementations

Figure 2:
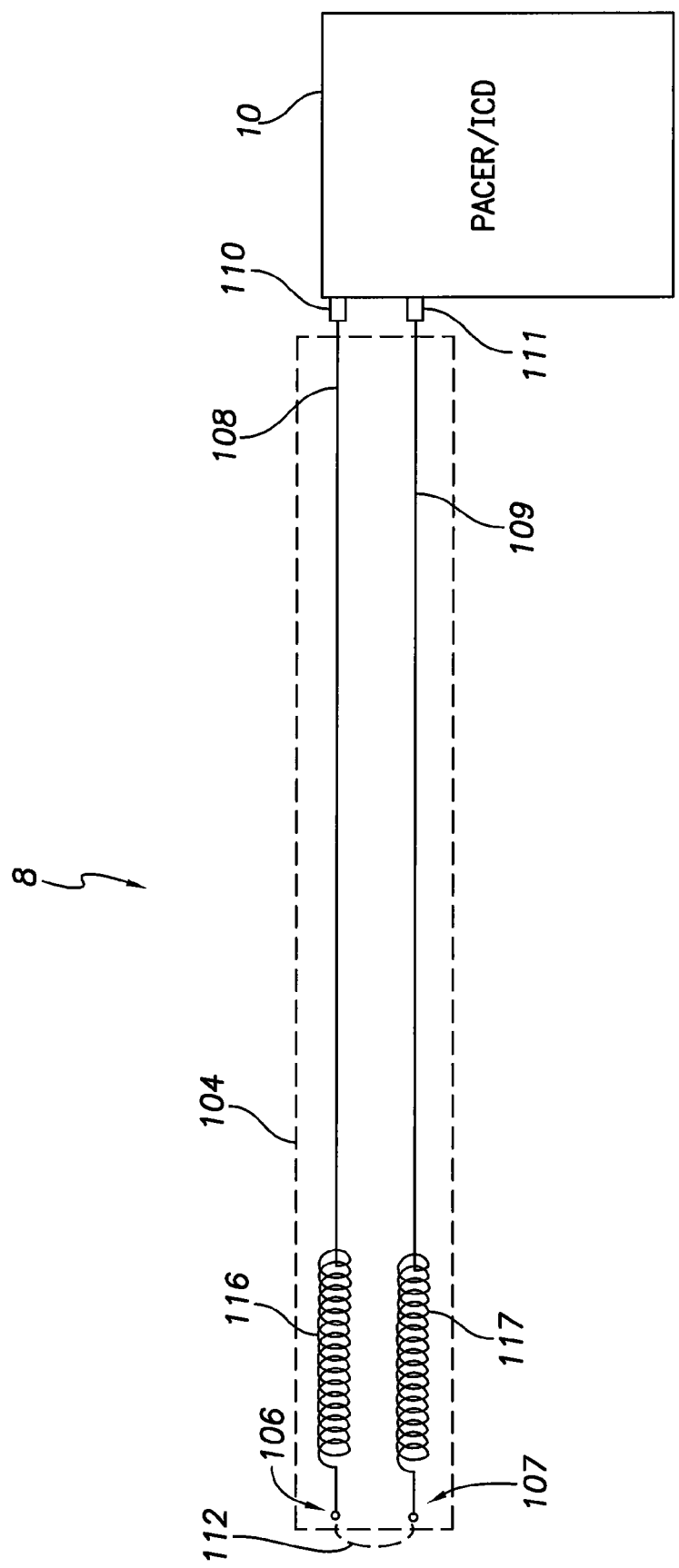
FIG. 2 is a block diagram, partly in schematic form, illustrating a bipolar embodiment for use as one of the leads of FIG. 1, wherein insulated coils are formed along distal ends of the conductors of the lead to provide inductive RF bandstop filtering so as to reduce heating of the lead during an MRI, and also illustrating a pacer/ICD connected to the lead.

FIG. 2 illustrates a bipolar example of one of the leads of FIG. 1 (shown schematically without any coiling or wrapping of the proximal end of the lead around the device as in FIG. 1.) More specifically, the figure shows an implantable system 8 having a pacer/ICD or other implantable medical device 10 with a bipolar lead 104. The bipolar lead includes a tip electrode 106 electrically connected to the pacer/ICD via a tip conductor 108 coupled to a tip connector or terminal 110 of the pacer/ICD. Conductor 108 includes, near its distal end, an insulated coil portion 116 formed as an inductive bandstop filter for filtering RF signals associated with MRIs. The bipolar lead also includes a ring electrode 107 electrically connected to the pacer/ICD via a ring conductor 109 coupled to a ring connector or terminal 111 of the pacer/ICD. The ring conductor includes an insulated coil portion 117 near its distal end. As with coil portion 116 of the tip conductor, the insulated coil of the ring conductor is provided to function as an inductive bandstop filter for filtering RF signals associated with MRIs.

Note that, in FIG. 2, the tip and ring conductors are shown schematically as being side-by-side. Depending upon the actual implementation, the tip conductor might be positioned inside the ring conductor (as with a coaxial lead) or might be physically positioned side-by-side (as with a co-radial lead.) The size, shapes and electrical parameters of the coil portions of the lead conductors can be configured so as to impede the conduction of signals at selected RF frequencies, such as at about 64 MHz or about 128 MHz. Preferably, the insulated coil portions of the conductors are configured to provide high impedance (preferably 1000 ohms or more) at one or more selected RF signal frequencies.

The insulated coils are formed or positioned near the distal ends of the leads, in part, to avoid the aforementioned coiling effect problems. By positioning the insulated coils at the distal ends, no significant shunt capacitance is developed between the insulated coils and the device housing, even if the proximal end of the lead is wrapped around the device during implant by the clinician (as in FIG. 1.) It is believed that avoiding shunt capacitance with the device housing has the effect, depending upon the particular lead, of reducing heating within the lead due to strong RF fields, such as those used during MRI procedures. As explained above, such heating can damage patient tissue and interfere with pacing and sensing.

Although the distal end of the lead is preferred, in other examples, the insulated coil portions of the tip and ring conductors can be positioned or formed elsewhere along the length of the lead, such as at its proximal end, or at multiple sites at about ¼ wavelength spacing along the conductors. See FIG. 17 below. If any of the insulated coils are formed or positioned at the proximal end of the lead, preferably additional features are employed to block shunt capacitance to avoid the aforementioned coiling effect problems. In this regard, U.S. patent application Ser. No. 12/537,916, of Min et al., entitled "Implantable Medical Device Lead Incorporating a Conductive Sheath Surrounding Insulated Coils to Reduce Lead Heating during MRI" (A09P1043) describes leads wherein conducting sheaths are providing along the proximal ends of the leads to permit insulated coils to be used at the proximal ends of the leads while avoiding coiling effect problems.

Note that, depending upon the particular implementation, during pacing/sensing, the tip electrode may be more negative than the ring, or vice versa. A conducting path 112 between tip electrode 106 and ring electrode 107 is provided through patient tissue (typically cardiac tissue.)

Figure 3:
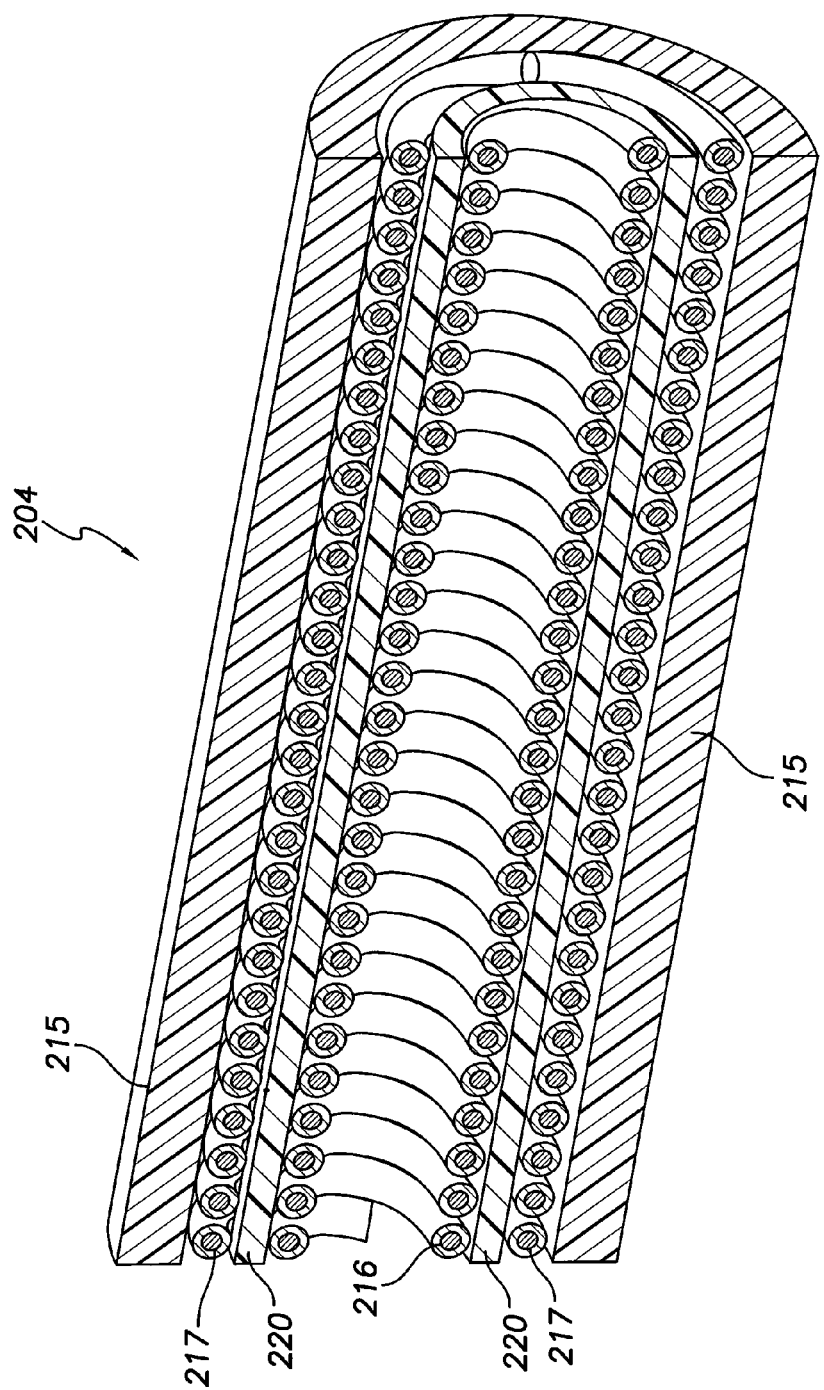
FIG. 3 is a perspective cross-sectional view of an alternative coaxial embodiment of the bipolar lead of FIG. 1, particularly illustrating nested inner and outer insulated coils for use as a bandstop filter.

FIG. 3 illustrates a coaxial implementation of the insulated coil bandpass filter of the invention. Coaxial lead 204 includes an insulated coil tip conductor 216 nested within an insulated coil ring conductor 217 (wherein the insulated coils are again configured to function as inductive bandstop filters for filtering RF signals.) Techniques for determining preferred parameters for configuring the insulated coils—such as their length, diameter and number of turns—are discussed below for use in achieving adequate impedance at selected the RF signal frequencies. An intermediate insulator 220 is positioned between the tip and ring coils. An external sleeve or sheath 215 encloses both the tip and ring coils. In this example, both the intermediate insulator and the external sleeve are non-conducting insulators. Examples are described below wherein conducting polymers are selectively employed.

Figure 4:
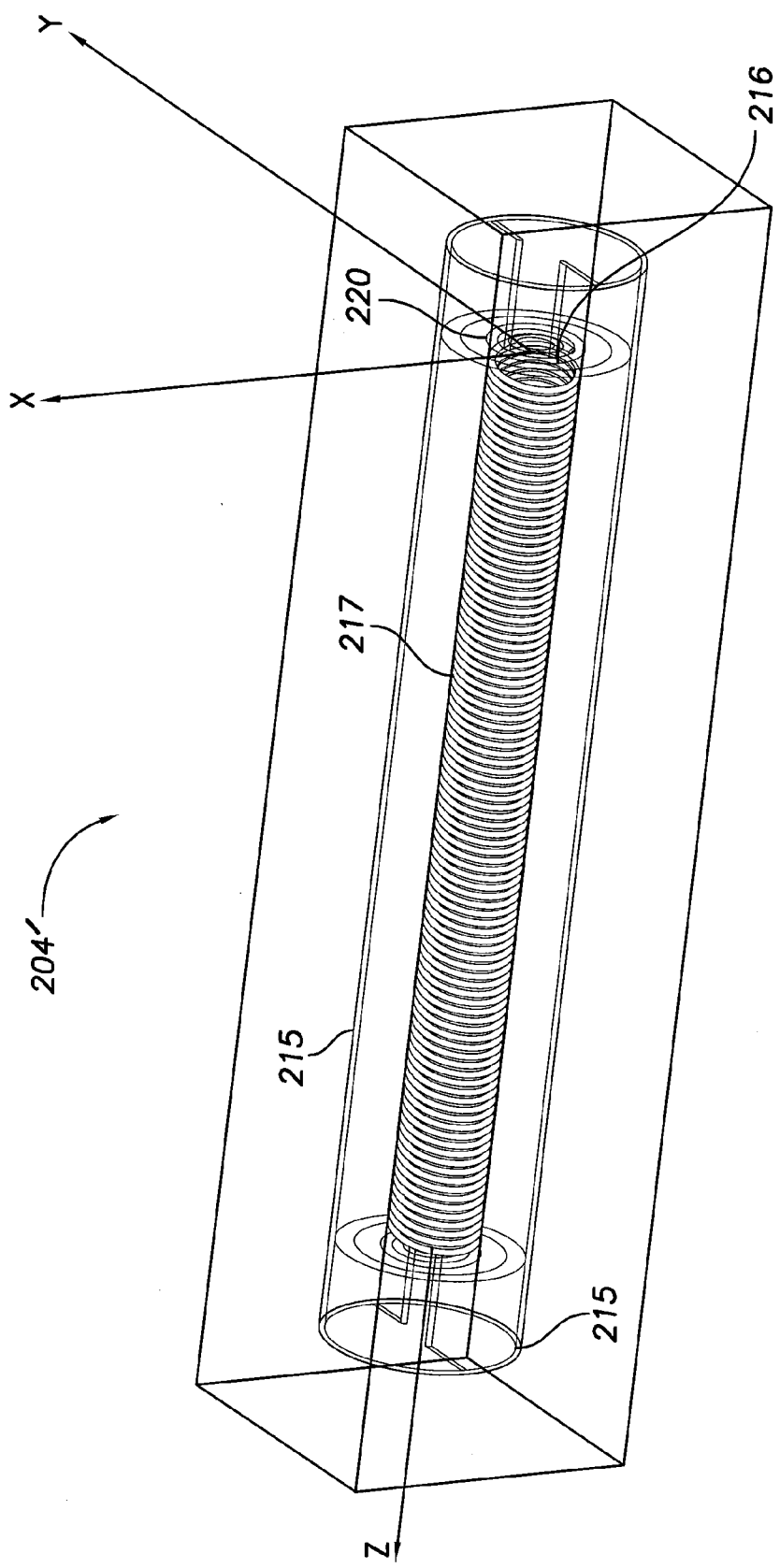
FIG. 4 is a 3D model of the inner and outer coils of the coaxial coil bandstop filter of FIG. 3.
Figure 5:
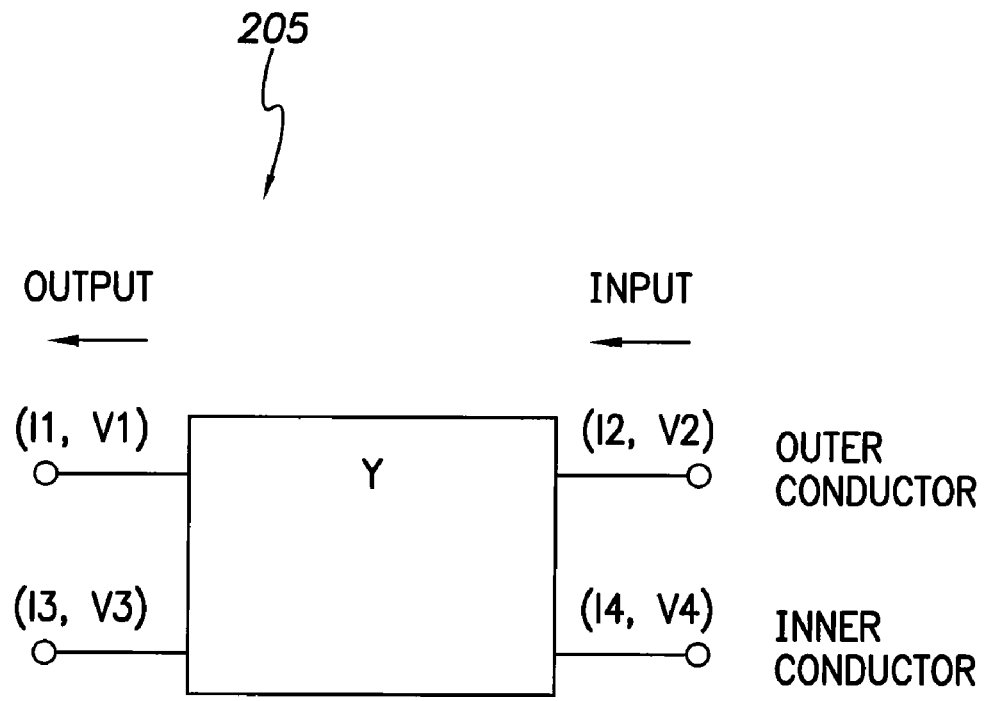
FIG. 5 illustrates a 4-port network representation of the coaxial coil bandstop filter of FIG. 3.
Figure 6:
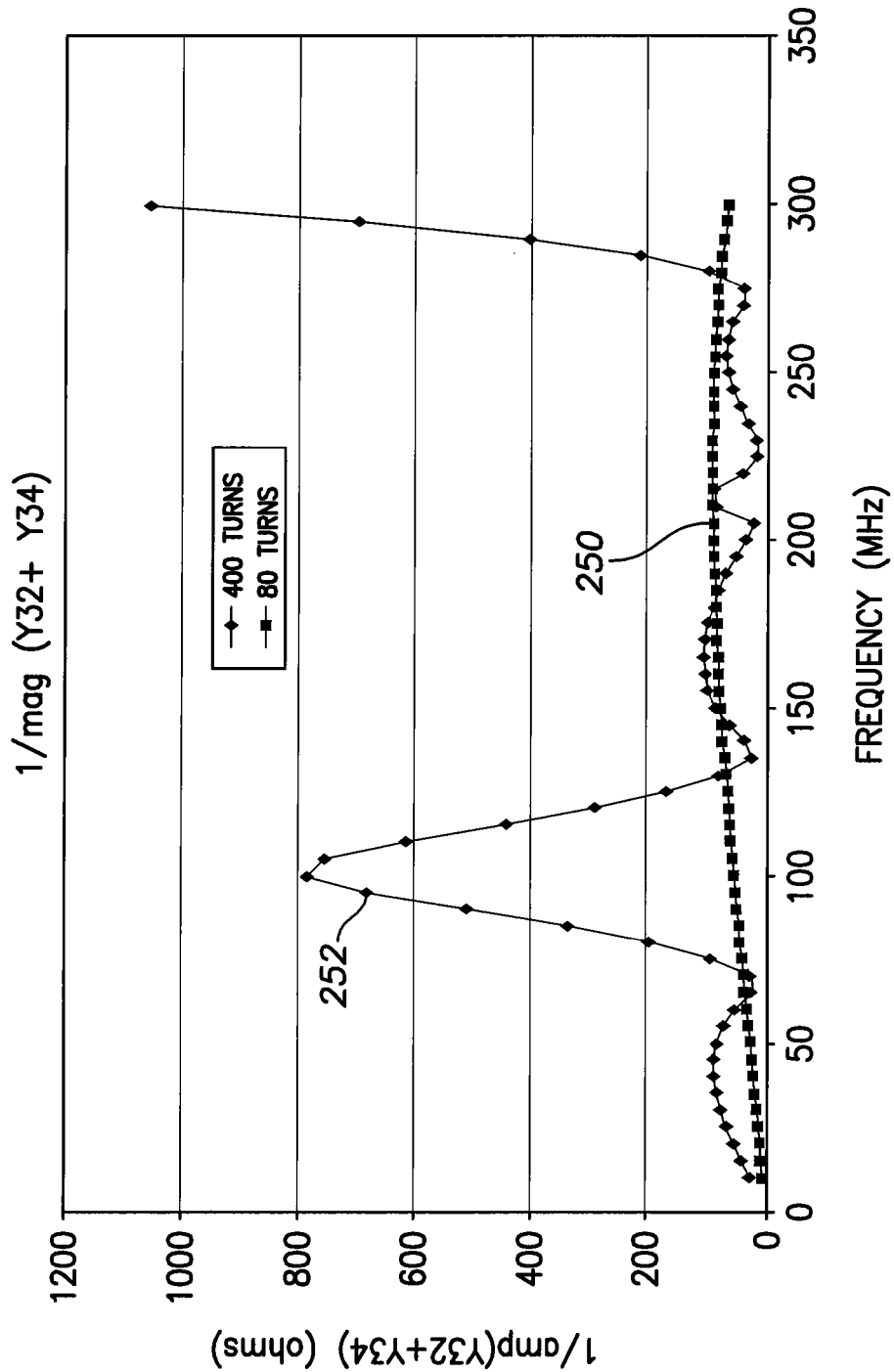
FIG. 6 is a graph illustrating frequency responses for exemplary coaxial coil bandstop filter implementations of 80 turns and 400 turns, respectively, derived using the 4-port network representation of FIG. 5.

FIG. 4 illustrates a 3D schematic model 204' of the nested inductive bandpass filter design of FIG. 3 for an 80-turn implementation of the filter. FIG. 5 provides a 4-port network representation 205 of the filter. FIG. 6 provides frequency response modeling results derived using the 4-port network for both an 80-turn and a 400-turn implementation.

More specifically, in the example of FIG. 4, the inner and outer coils 216 and 217 of the filter both have lengths of 1.2 cm and 80 turns. The pitch is 6 mil (wherein one mil is one thousandth of an inch.) The overall length of the coils is 489 mil. The inner coil 216 has an inner diameter (ID) of 19 mils. The ID of the outer coil 217 is 43 mils. An ethylene tetrafluoroethylene (ETFE) coating of 1.5 mils is provided on the turns of the coils to insulate the turns. Alternatively, polytetrafluoroethylene ("PTFE"), silicone rubber, silicone rubber polyurethane copolymer ("SPC") can be used. The external sleeve 215 is a shrink tube formed of silicone or Optim® having an outer diameter (OD) of 78 mils. (Optim is a registered trademark of Pacesetter, Inc. DBA St. Jude Medical Cardiac Rhythm Management Division. Optim refers to a silicone-polyurethane co-polymer insulation created specifically for cardiac leads. The new material blends the biostability and flexibility of silicone with the durability, lubricity and abrasion-resistance of polyurethane.) Alternatively, materials such as polyurethane can be used in the external sleeve.

The intermediate insulator 220 is formed of silicone or Optim and has an OD of 41 mils. For a 400-turn implementation, the parameters are the same, except the overall length, which is 5*489 mil. [Note that FIG. 4 also illustrates a 3D block surrounding the model itself. This block is provided merely for model borders and is not a part of the structure of the lead.]

In the 4-port network 205 of FIG. 5, "I" represents current, "V" represents voltage, and "Y" represents admittance (i.e. the reciprocal of impedance "Z"). Admittance is specified between various pairs of nodes. For example, Y12 represents the admittance between node 1 (the output node of the outer coil) and node 2 (the input node of the outer coil.) The equations of FIG. 5 specify the current (I) at each node. To achieve band stop filtering, it is desirable to make I3 small at MRI RF (despite the effects of coupling and other factors.) This can be achieved by controlling the relationship between V2 and V4. One suitable method is to make V2=V4. With V2=V4; V1=V3=0; then I3=Y32* V2+Y34*V4=(Y32+Y34)*V4, leading to:

$$Z43 = V4/I3 = 1/(Y32+Y34)$$

where Z43 represents the impedance along the tip conductor through the inner coil. It is this impedance value that preferably reaches the target impedance of 1000 ohms at MRI RF. The resulting frequency response curve for Z43 [specified as 1/mag (Y32+Y34)] is shown in FIG. 6 for both an 80-turn and a 400-turn implementation.

In FIG. 6, the frequency response for the 80-turn model is represented by way of curve 250. The frequency response for the 400-turn model is illustrated by way of curve 252. For both curves, the vertical scale is impedance in units of ohms. As can be seen, the 400-turn inductive coil filter achieved a maximum impedance of about 800 ohms at about 100 MHz. The 80-turn inductive coil filter achieved a maximum impedance of only about 100 ohms at about 200 MHz. Based on these results, the 400-turn coil provides sufficient impedance to achieve a substantial degree of inductive bandstop filtering at some RF signal frequencies [though not at the particular frequencies associated with MRIs (of about 64 MHz and about 128 MHz) and not quite reaching the target impedance that is preferred (i.e. >1000 ohms.)] Nevertheless, for at least some filtering applications, the 400-coil inductive coaxial filter modeled in FIG. 4 may be sufficient. The 80-turn coil filter shown by way of curve 250 provided substantially less impedance, thus emphasizing the need to either provide a greater number of turns or to provide some form of capacitive shunting or to optimize design parameters to increase impedance at selected frequencies.

In the following sections, various inductive-capacitive filter implementations are described and modeled, which can achieve greater impedance at the RF signal frequencies of MRIs.

Figure 7:
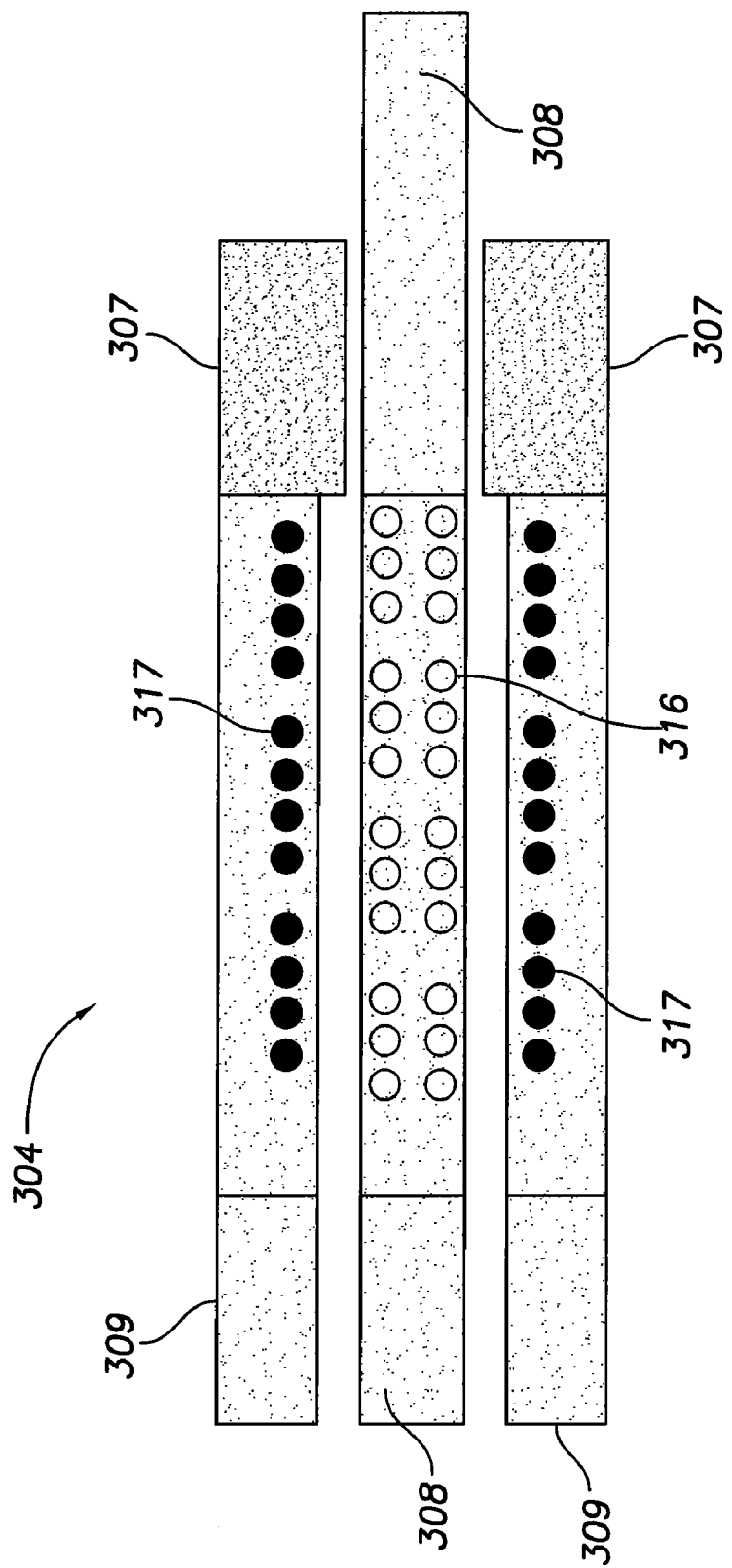
FIG. 7 is a simplified side cross-sectional view of a portion of an alternative coaxial embodiment of the bipolar lead of FIG. 1, wherein the ring electrode of the lead is configured to provide capacitive shunting to the tip conductor to improve bandstop filtering.

FIG. 7 illustrates a coaxial implementation wherein the ring electrode is configured to achieve a degree of capacitive coupling with the tip conductor to provide capacitive shunting at RF so as to improve impedance at MRI RF. More specifically, FIG. 7 shows a coaxial lead 304 with an outer insulated coil 317 (formed along outer, ring conductor 309) and an inner insulated coil 316 (formed along inner, tip conductor 308.) The outer insulated coil is coupled to ring electrode 307. The ring electrode is configured to be generally longer than the typical coaxial lead ring electrode and to have a smaller inner diameter. The smaller inner diameter places the inner surface of the ring electrode in relatively close proximity to the tip conductor. The greater length provides for a relatively larger capacitive surface. Both serve to increase the degree of capacitive coupling at RF so as to provide some shunting of RF signals. This has the effect of converting the inductive coil bandstop filter into an inductive-capacitive filter, which achieves greater impedance at RF.

Otherwise routine testing and experimentation may be performed to determine preferred parameters for configuring the ring electrode—such as its inner diameter and its length—for use in a particular lead so as to achieve a desired impedance at particular RF signal frequencies, such as those of MRIs. In one example, the length of the ring electrode is in the range of 2-6 millimeters (mm). The ID of the ring is in the range of about 31-50 mils. Note also that FIG. 7 is a simplified view that shows only selected components of the lead and does not illustrate all features or components, such as the outer sheath of insulation, etc.

Figure 8:
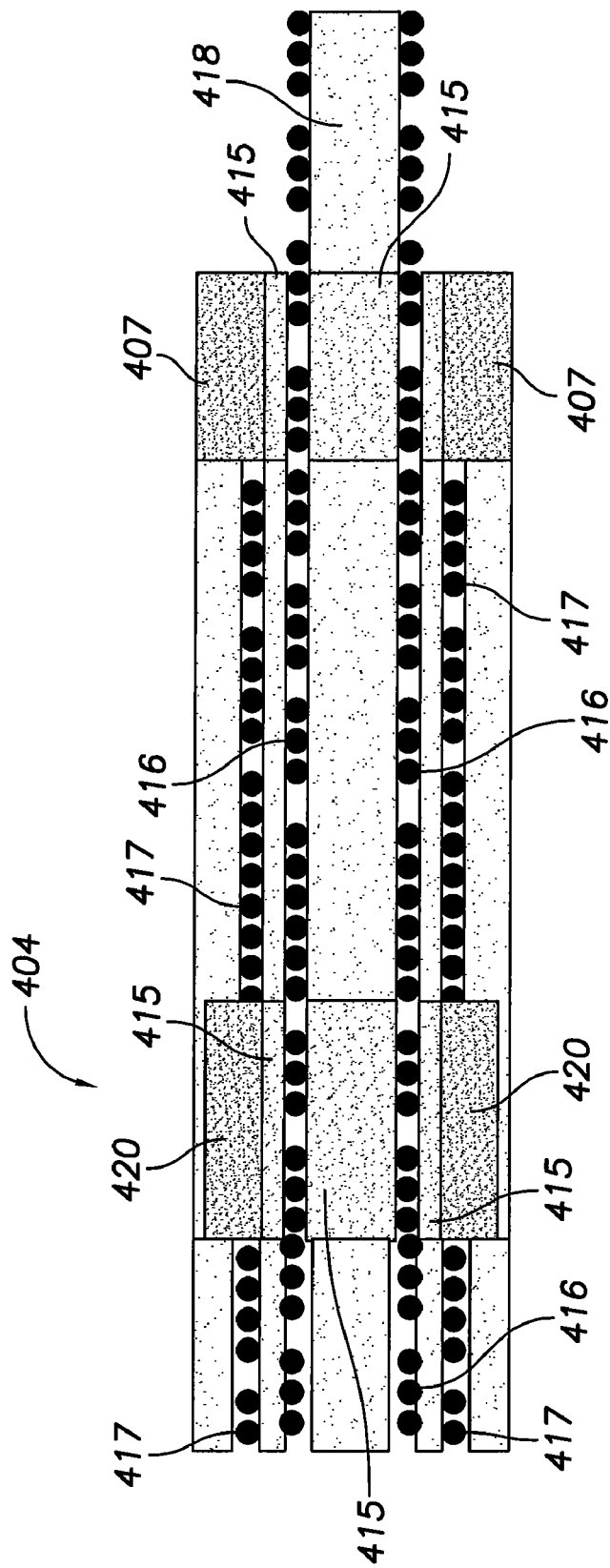
FIG. 8 is a simplified side cross-sectional view of a portion of yet another coaxial embodiment of the bipolar lead of FIG. 1, wherein a capacitive transition is provided between the insulated coil of the ring conductor and proximal portions of the ring conductor to provide further capacitive shunting to improve bandstop filtering.

FIG. 8 illustrates an alternative coaxial implementation providing capacitive coupling wherein an additional capacitive transition is employed. Coaxial lead 404 has an outer insulated coil 417 and an inner insulated coil 416. The outer insulated coil is coupled to ring electrode 407. As with the embodiment of FIG. 7, the ring is configured to provide some capacitive shunting of RF signals. Additionally, an embedded capacitive transition 420 is provided along the outer coil 417 at a location proximal the ring electrode (which may be embedded as shown or exposed to patient tissues.) A conducting polymer 415 for use in RF shunting is provided between component 420 and inner coil 416 at the location of component 420. Additional conducting polymer 415 is provided inside inner coil 416 also at the location of component 420. Still more of the conducting polymer is provided between the ring electrode 407 and the inner coil 416 (at the location of the ring electrode) and interior to the inner coil (again also at the location of the ring electrode.) The capacitive transition 420 in combination with the various polymer components 415 serves to further increase the degree of capacitive coupling at RF so as to provide improved shunting of RF signals. That is, RF signals are shorted or decoupled. Otherwise routine testing and experimentation may be performed to determine preferred parameters for configuring the capacitive transition—such as its length in a range of 2-4 mm—for use in a particular lead so as to achieve a desired impedance at particular RF signal frequencies, such as those of MRIs. Note also that inner tubing 418 is provided inside the inner coil.

In terms of the 4-port network analysis above, the provision of capacitive shunting (sufficient to short RF) results in the Z43 being equal 1/Y34 rather than 1/(Y32+Y34). [Again, Z43 is the impedance along the tip conductor through the inner coil.)

Figure 9:
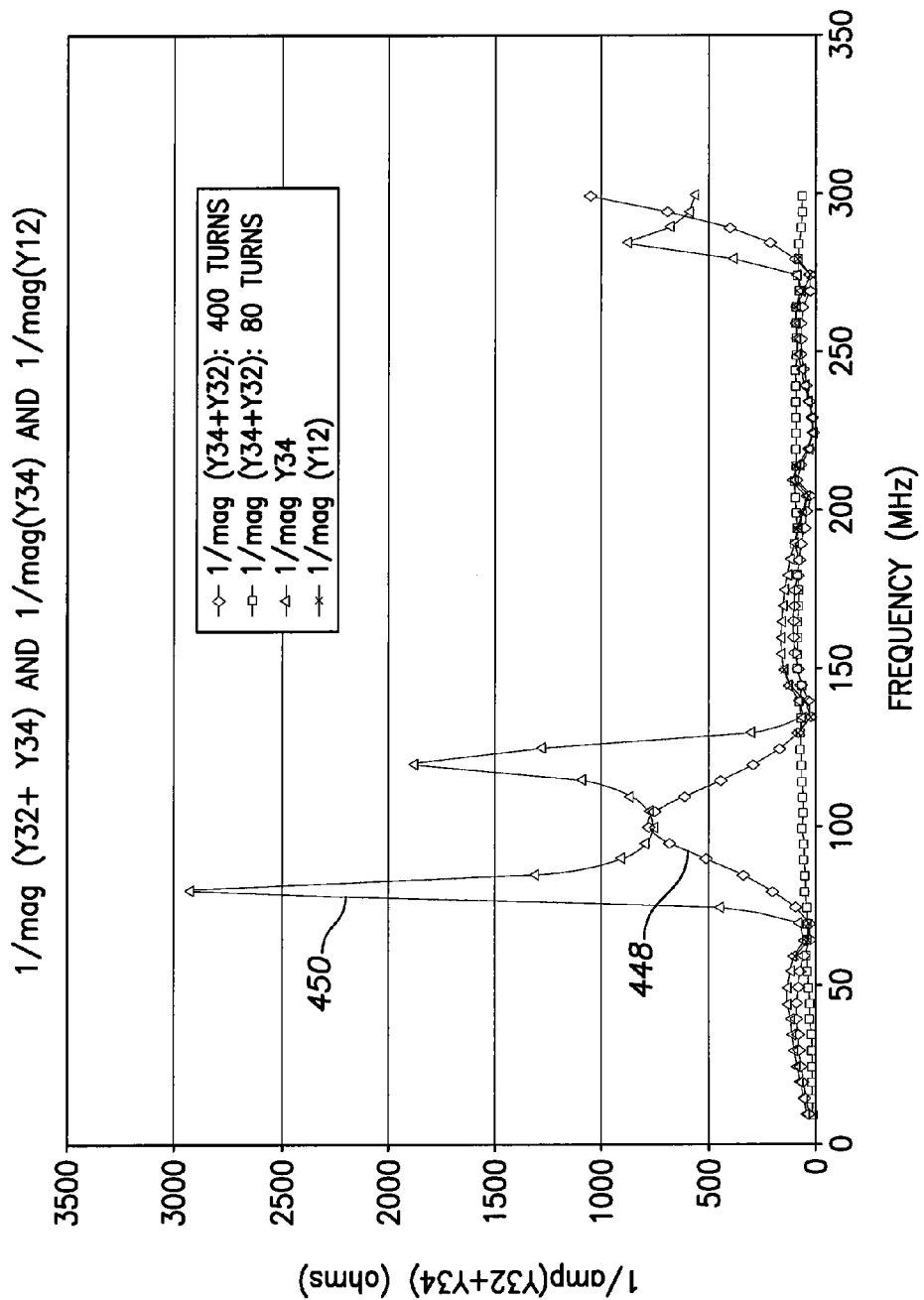
FIG. 9 is another graph illustrating frequency responses for exemplary coaxial coil bandstop filter implementations derived using the 4-port network representation of FIG. 5, demonstrating higher impedance achieved using capacitive shunting.

FIG. 9 provides frequency response modeling results derived using the 4-port network for the 80-turn and 400-turn implementation models (both with and without RF shunting.) Curve 448 represents the frequency response with capacitive shunting between inner and outer coils at both ends and shunting to fluid at one end for a 400-turn model. Curve 450 illustrates the frequency response with RF shunting to fluid at both ends for a 400-turn model. As can be seen, the 400-turn inductive/capacitive coil filter achieved an impedance of nearly 3000 ohms at about 64 MHz and an impedance of nearly 2000 ohms at about 128 MHz. This is typically sufficient to achieve a substantial amount of heat reduction within the lead during MRIs. If more heating reduction is needed, higher impedance can be achieved by lead parameter optimization or longer coil length. (Note that, within the figure, some additional curves are shown, which are not important to the present discussion.)

Figure 10:
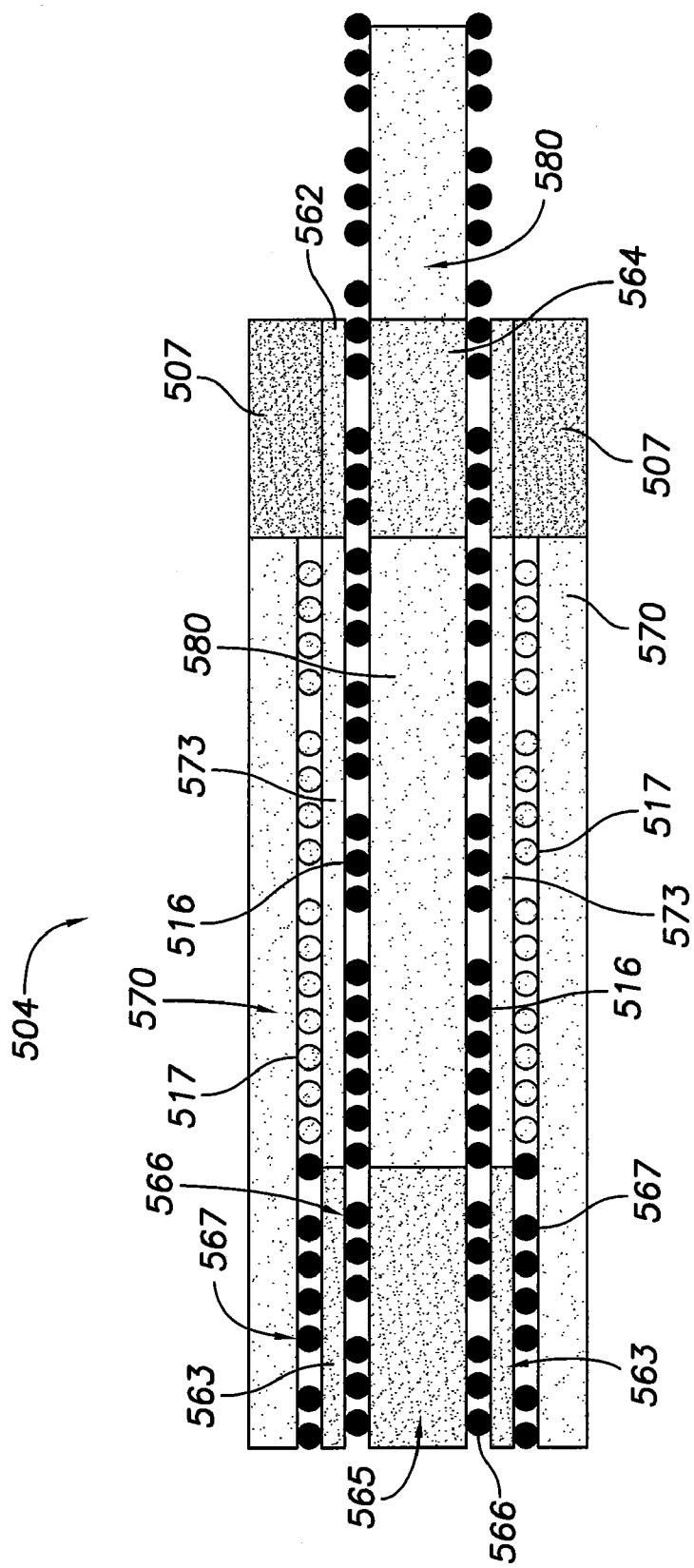
FIG. 10 is a simplified side cross-sectional view of a portion of another coaxial embodiment of the bipolar lead of FIG. 1, wherein a polymer tubing separator and an inner polymer tubing core are provided.

FIG. 10 illustrates a coaxial implementation employing either dielectric material with high permittivity or conducting polymers to improve RF shunting. Coaxial lead 504 has an outer insulated coil 517 (formed along outer, ring conductor, not shown) and an inner insulated coil 516 (formed along inner, tip conductor, not shown.) At its distal end, the outer insulated coil is coupled to ring electrode 507. An outer conducting polymer or high dielectric material 562 is positioned between ring electrode 507 and adjacent turns of coil 516. Note that, in this embodiment, inner coil 516 extends under the ring electrode toward the distal end of the lead. An inner conducting polymer or high dielectric material 564 is positioned inside the inner coils at the same location along the lead as ring 507 and outer polymer 562.

At the opposing proximal end of the coils, a second set of inner and outer conducting polymers or high dielectric material are provided 563 and 565. Here, outer polymer or dielectric 563 is positioned between the inner and outer coils. Inner polymer 565 is inside the inner coils at the same location along the lead as outer polymer 563. The various conducting polymers provide for some degree of RF shorting so as to improve the function of the inductive coils.

FIG. 10 also illustrates an inner non-conducting core 580 provided inside the inner coils (at locations where there is no inner conducting polymer.) An insulating separator 573 is provided between the inner and outer coils (at locations where there are no conducting polymers.) An outer sheath or insulator 570 is also shown, mounted around the outer coils. Although not shown, a similar outer insulator may be provided along the inner coils at points distal to the ring electrode 507. Note, also, that turns of the inner and outer coils that are adjacent components 563 and 565 need not be insulated. To distinguish these turns from the other turns of the coils (which are insulated), the un-insulated coil turns are denoted by reference numerals 567 and 566.

In general, the conducting polymers serve to increase the degree of capacitive coupling as an alternative method to insulation layer with high dielectric constant at RF so as to provide improved shunting of RF signals. In this regard, the conducting polymers reduce dB/dt flux through the coils. Otherwise routine testing and experimentation may be performed to determine preferred parameters for configuring the conducting polymers—such as their inner diameters, lengths and compositions/density of metallic power—for use in a particular lead so as to achieve a desired impedance at particular RF signal frequencies, such as those of MRIs. However, it should be understood that insulation layers of high dielectric material can be used rather than the conducting polymer layers.

Figure 11:
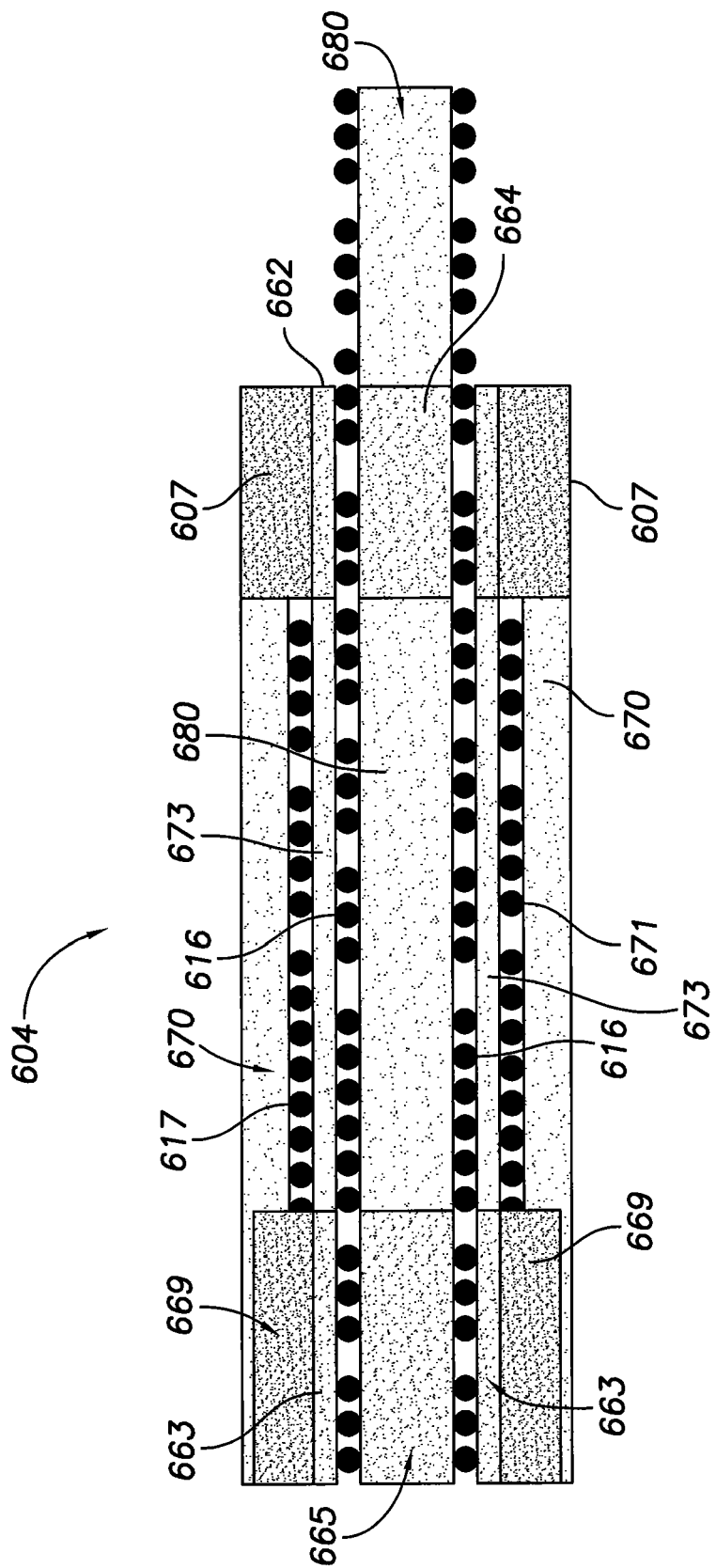
FIG. 11 is a simplified side cross-sectional view of a portion of yet another coaxial embodiment of the bipolar lead of FIG. 1, wherein polymer tubing and a polymer core is also provided.

FIG. 11 illustrates a coaxial implementation employing both a capacitive transition and a set of conducting polymers or insulation layers. Many of the features of the lead of FIG. 11 are the same as those of FIG. 10 and only pertinent differences will be described in detail. Coaxial lead 604 has an outer insulated coil 617 and an inner insulated coil 616. At its distal end, the outer insulated coil is coupled to ring electrode 607, besides using insulation layers with conducting polymers 662 and 664 provided to improve shunting between the ring electrode and the inner coils. At the opposing proximal end of the coils, a capacitive transition 669 is provided, similar to the one described above with reference to FIG. 8. Inner and outer conducting polymers or insulation layers 664 and 665 are positioned, as shown, along the coils at the location of the capacitive transition. The various conducting polymers in combination with the capacitive transition improve RF shunting so as to improve the function of the inductive coils.

As with the lead of FIG. 10, lead 604 also includes an inner, non-conducting core 680 provided inside the inner coils, an insulating separator 673 is provided between the inner and outer coils, and an outer sheath or insulator 670 is provided. Again, otherwise routine testing and experimentation may be performed to determine preferred parameters for configuring the capacitive transition and the conducting polymers or insulation layers—such as their sizes and compositions/density of metallic power—for use in a particular lead so as to achieve a desired impedance at particular RF signal frequencies, such as those of MRIs.

Figure 12:
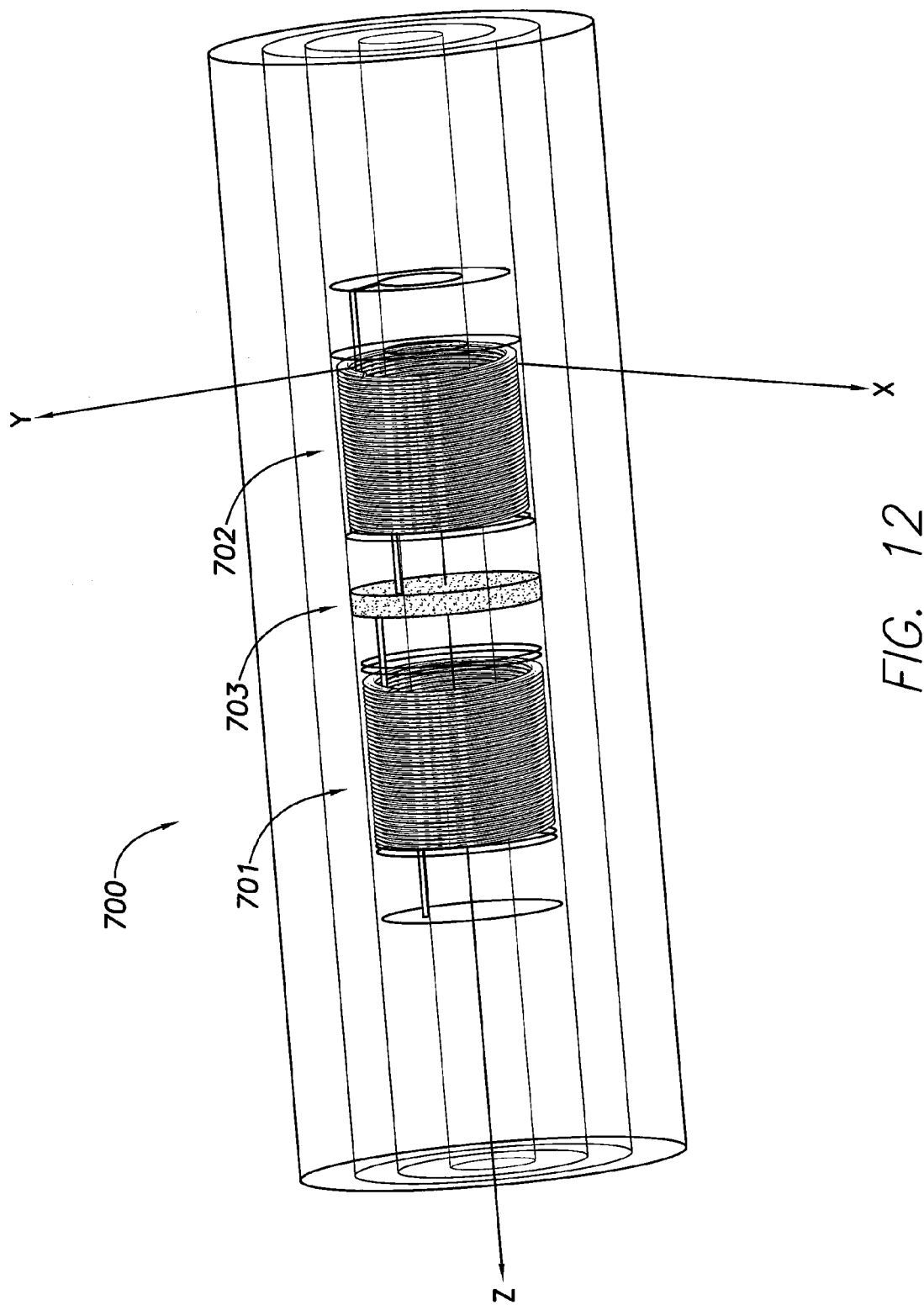
FIG. 12 is a 3D model illustrating inner and outer coils of alternative coaxial embodiment to that of FIG. 4, wherein two pairs of coils are provided.

FIG. 12 illustrates a 3D schematic model 700 of a set of inductive bandpass filters. In this example, first and second insulated coil bandpass filters 701 and 702 are connected through a conducting polymer ring 703. The two filters are configured to provide different SRFs. In general, multiple segments can be used at SRFs designed as RF1, RF2, . . . , RFn. For example, RF1=64 MHz and RF2=128 MHz (n=2). Each segment can be isolated (magnetically) for RF shorting via one or more conducting polymers as shown.

Figure 13:
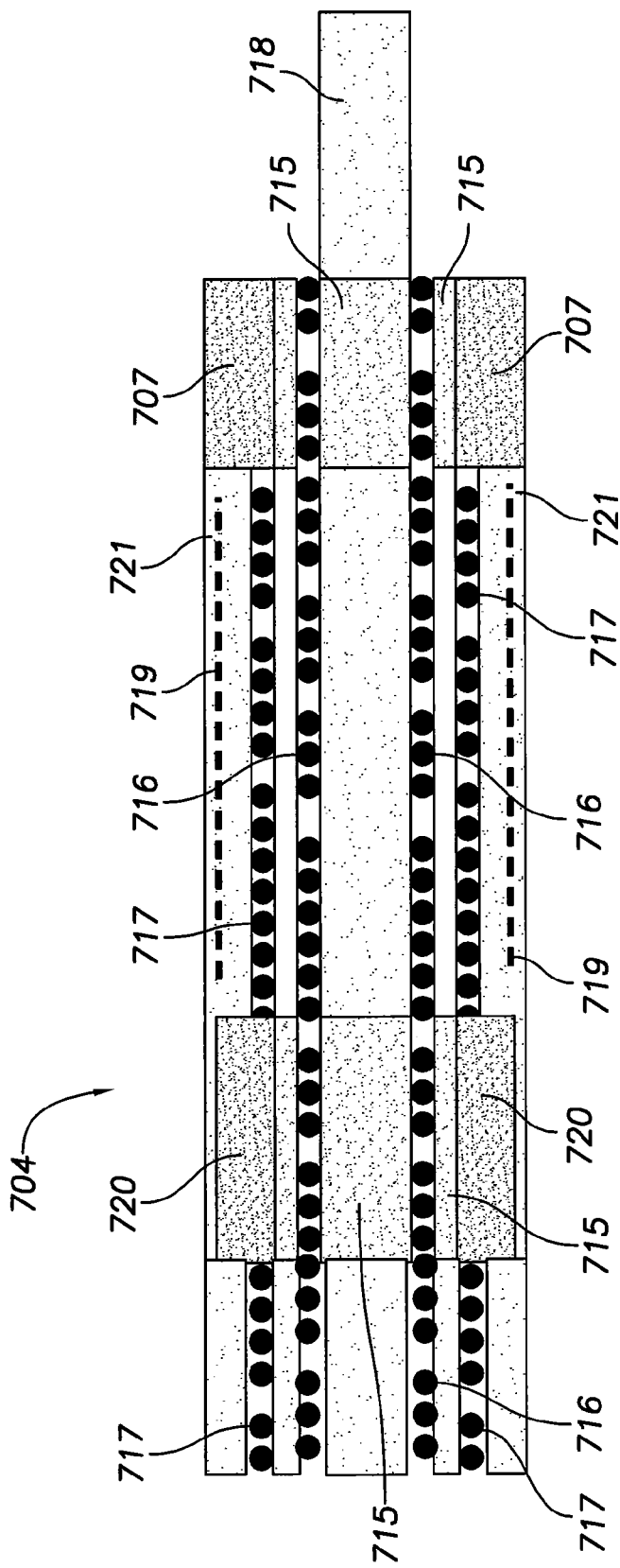
FIG. 13 is a simplified side cross-sectional view of a portion of yet another coaxial embodiment of the bipolar lead of FIG. 1, wherein shielding is provided adjacent the ring electrode, with the shielding material embedded in a sleeve or outer insulation coating of the lead.
Figure 14:
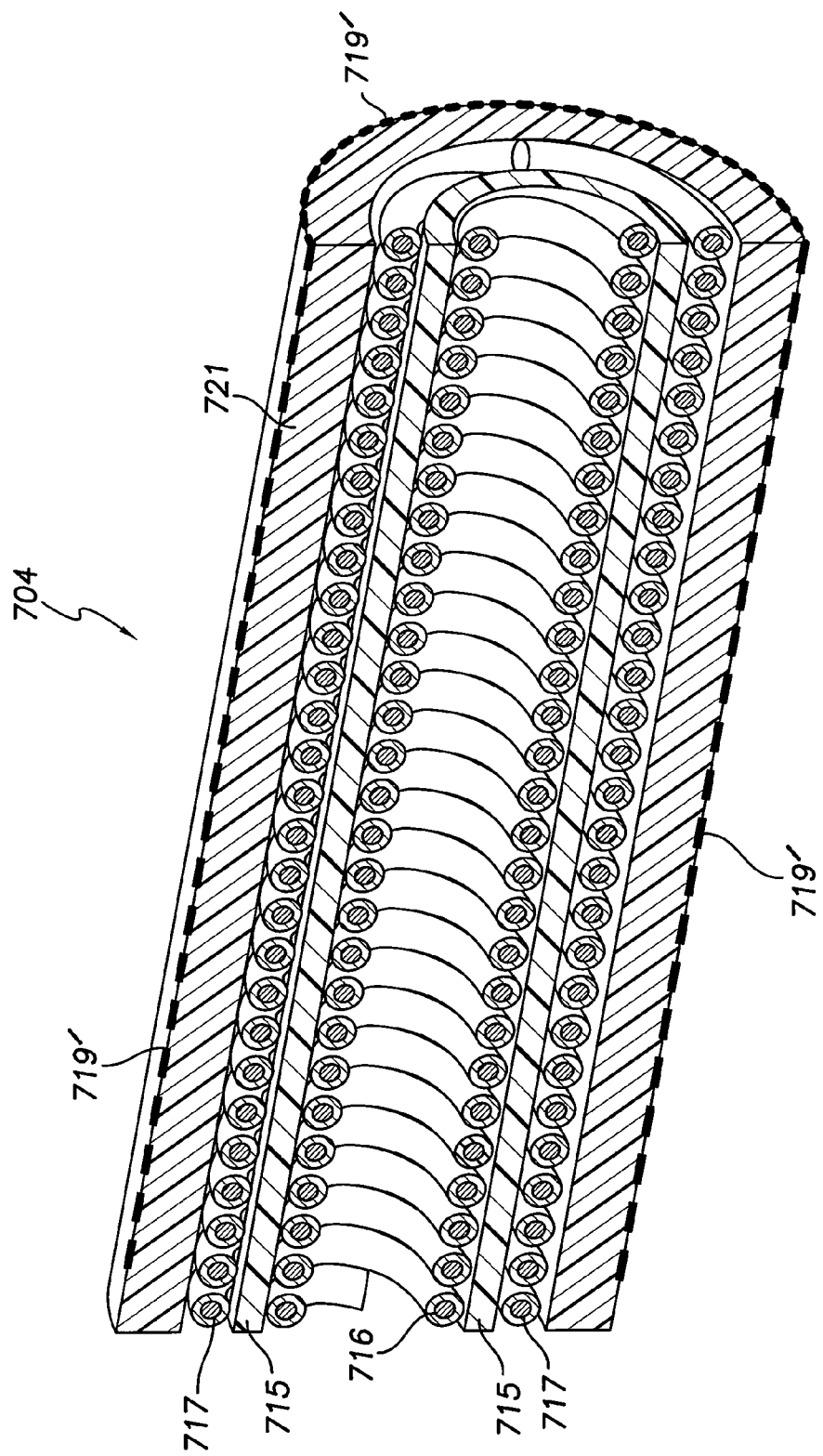
FIG. 14 is a perspective cross-sectional view of another alternative coaxial embodiment of the lead of FIG. 13, with the shielding material mounted on the outer surface of the lead.

FIGS. 13 and 14 illustrate an alternative coaxial implementation providing capacitive coupling wherein shielding is employed adjacent the ring electrode. This implementation is similar to the implementation of FIG. 8 but lead 704 of FIG. 13 includes a shielding layer 719 embedded within an insulator layer 721 formed adjacent to (and proximal from) ring electrode 707. Alternatively, as shown in FIG. 14, the shielding layer 719' may be on the outer surface of the sleeve or coating of the lead. The shielding layer may be, e.g., a metal mesh or a conducting polymer tube incorporating non-ferrous metal powders. See, the patent application cited above of Min et al. entitled "Implantable Medical Device Lead Incorporating a Conductive Sheath Surrounding Insulated Coils to Reduce Lead Heating during MRI."

For the sake of completeness, the other components of the lead of FIG. 13 are as follows: Coaxial lead 704 has an outer insulated coil 717 and an inner insulated coil 716. The outer insulated coil is coupled to ring electrode 707. Additionally, an embedded capacitive transition 720 is provided along the outer coil 717 at a location proximal the ring electrode (which may be embedded as shown or exposed to patient tissues.) A conducting polymer 715 for use in RF shunting is provided between component 720 and inner coil 716 at the location of component 720. Additional conducting polymer 715 is provided inside inner coil 716 also at the location of component 720. Still more of the conducting polymer is provided between the ring electrode 707 and the inner coil 716 (at the location of the ring electrode) and interior to the inner coil (again also at the location of the ring electrode.) Inner tubing 718 is provided inside the inner coil.

FIG. 14

The various configurations described above can be exploited for use with a wide variety of implantable medical systems. For the sake of completeness, a detailed description of an exemplary pacer/ICD and lead system will now be provided.

Exemplary Pacer/ICD/Lead System

FIG. 15 provides a simplified diagram of the pacer/ICD of FIG. 1 (shown without any coiling of the leads around the pacer/ICD.) The pacer/ICD is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 812 by way of a right atrial lead 820 having an atrial tip electrode 822 and an atrial ring electrode 823 implanted in the atrial appendage. Pacer/ICD 10 is also in electrical communication with the heart by way of a right ventricular lead 830 having, in this embodiment, a ventricular tip electrode 832, a right ventricular ring electrode 834, a right ventricular (RV) coil electrode 836. Typically, the right ventricular lead 830 is transvenously inserted into the heart so as to place the RV coil electrode 836 in the right ventricular apex. Accordingly, the right ventricular lead is capable of receiving cardiac signals, and delivering stimulation in the form of pacing and shock therapy to the right ventricle. An insulated coil bandpass filter 816, configured as described above, is positioned within and along distal portions of lead 830 so as to reduce lead heating. The filter is shown in phantom lines, as it is internal to the lead. Although not shown, a similar insulated coil bandpass filter may be provided within RA lead 820.

To sense left atrial and ventricular cardiac signals and to provide left chamber pacing therapy, pacer/ICD 10 is coupled to a "coronary sinus" lead 824 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 824 is designed to receive atrial and ventricular cardiac signals and to deliver left ventricular pacing therapy using at least a left ventricular tip electrode 826 and a left ventricular ring electrode 829 and to deliver left atrial pacing therapy using at least a left atrial ring electrode 827, and shocking therapy using at least an SVC coil electrode 828. An insulated coil bandpass filter 817, configured as described above, is positioned within and along distal portions of lead 824 so as to reduce lead heating. The filter is shown in phantom lines, as it is internal to the lead.

With this lead configuration, biventricular pacing can be performed. Although only three leads are shown in FIG. 15, it should also be understood that additional stimulation leads (with one or more pacing, sensing and/or shocking electrodes) may be used in order to efficiently and effectively provide pacing stimulation to the left side of the heart or atrial cardioversion and/or defibrillation. The filters reduce lead heating during MRIs or in the presence of other sources of strong RF fields.

A simplified block diagram of internal components of pacer/ICD 10 is shown in FIG. 14. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 840 for pacer/ICD 10, shown schematically in FIG. 14, is often referred to as the "can", "case" or "case electrode" and may be programmably selected to act as the return electrode for all "unipolar" modes. The housing 840 may further be used as a return electrode alone or in combination with one or more of the coil electrodes, 828, 836 and 838, for shocking purposes. The housing 840 further includes a connector (not shown) having a plurality of terminals, 842, 843, 844, 845, 846, 848, 852, 854, 856 and 858 (shown schematically and, for convenience, the names of the electrodes to which they are connected are shown next to the terminals). As such, to achieve right atrial sensing and pacing, the connector includes at least a right atrial tip terminal ($A_R$ TIP) 842 adapted for connection to the atrial tip electrode 822 and a right atrial ring ($A_R$ RING) electrode 843 adapted for connection to right atrial ring electrode 823. To achieve left chamber sensing, pacing and shocking, the connector includes at least a left ventricular tip terminal ($V_L$ TIP) 844, a left ventricular ring terminal ($V_L$ RING) 845, a left atrial ring terminal ($A_L$ RING) 846, and a left atrial shocking terminal ($A_L$ COIL) 848, which are adapted for connection to the left ventricular ring electrode 826, the left atrial tip electrode 827, and the left atrial coil electrode 828, respectively. To support right chamber sensing, pacing and shocking, the connector further includes a right ventricular tip terminal ($V_R$ TIP) 852, a right ventricular ring terminal ($V_R$ RING) 854, a right ventricular shocking terminal ($R_V$ COIL) 856, and an SVC shocking terminal (SVC COIL) 858, which are adapted for connection to the right ventricular tip electrode 832, right ventricular ring electrode 834, the RV coil electrode 836, and the SVC coil electrode 838, respectively.

At the core of pacer/ICD 10 is a programmable microcontroller 860, which controls the various modes of stimulation therapy. As is well known in the art, the microcontroller 860 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 860 includes the ability to process or monitor input signals (data) as controlled by a program code stored in a designated block of memory. The details of the design and operation of the microcontroller 860 are not critical to the invention. Rather, any suitable microcontroller 860 may be used that carries out the functions described herein. The use of microprocessor-based control circuits for performing timing and data analysis functions are well known in the art.

As shown in FIG. 14, an atrial pulse generator 870 and a ventricular pulse generator 872 generate pacing stimulation pulses for delivery by the right atrial lead 820, the right ventricular lead 830, and/or the coronary sinus lead 824 via an electrode configuration switch 874. It is understood that in order to provide stimulation therapy in each of the four chambers of the heart, the atrial and ventricular pulse generators, 870 and 872, may include dedicated, independent pulse generators, multiplexed pulse generators or shared pulse generators. The pulse generators, 870 and 872, are controlled by the microcontroller 860 via appropriate control signals, 876 and 878, respectively, to trigger or inhibit the stimulation pulses.

The microcontroller 860 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 874 includes a plurality of switches for connecting the desired electrodes to the appropriate I/O circuits, thereby providing complete electrode programmability. Accordingly, the switch 874, in response to a control signal 880 from the microcontroller 860, determines the polarity of the stimulation pulses (e.g., unipolar, bipolar, combipolar, etc.) by selectively closing the appropriate combination of switches (not shown) as is known in the art.

Atrial sensing circuits 882 and ventricular sensing circuits 884 may also be selectively coupled to the right atrial lead 820, coronary sinus lead 824, and the right ventricular lead 830, through the switch 874 for detecting the presence of cardiac activity in each of the four chambers of the heart. Accordingly, the atrial (ATR. SENSE) and ventricular (VTR. SENSE) sensing circuits, 882 and 884, may include dedicated sense amplifiers, multiplexed amplifiers or shared amplifiers. The switch 874 determines the "sensing polarity" of the cardiac signal by selectively closing the appropriate switches, as is also known in the art. In this way, the clinician may program the sensing polarity independent of the stimulation polarity. Each sensing circuit, 882 and 884, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain and/or sensitivity control enables pacer/ICD 10 to deal effectively with the difficult problem of sensing the low amplitude signal characteristics of atrial or ventricular fibrillation. The outputs of the atrial and ventricular sensing circuits, 882 and 884, are connected to the microcontroller 860 which, in turn, are able to trigger or inhibit the atrial and ventricular pulse generators, 870 and 872, respectively, in a demand fashion in response to the absence or presence of cardiac activity in the appropriate chambers of the heart.

For arrhythmia detection, pacer/ICD 10 utilizes the atrial and ventricular sensing circuits, 882 and 884, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "Fib-waves") are then classified by the microcontroller 860 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 890. The data acquisition system 890 is configured to acquire intracardiac electrogram signals, convert the raw analog data into a digital signal, and store the digital signals for later processing and/or telemetric transmission to an external device 902. The data acquisition system 890 is coupled to the right atrial lead 820, the coronary sinus lead 824, and the right ventricular lead 830 through the switch 874 to sample cardiac signals across any pair of desired electrodes. The microcontroller 860 is further coupled to a memory 894 by a suitable data/address bus 896, wherein the programmable operating parameters used by the microcontroller 860 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 894 through a telemetry circuit 900 in telemetric communication with an external device 902, such as a programmer, transtelephonic transceiver or a diagnostic system analyzer, or a bedside monitoring system. The telemetry circuit 900 is activated by the microcontroller by a control signal 906. The telemetry circuit 900 advantageously allows IEGMs and other electrophysiological signals and/or hemodynamic signals and status information relating to the operation of pacer/ICD 10 (as stored in the microcontroller 860 or memory 894) to be sent to the external programmer device 902 through an established communication link 904.

Pacer/ICD 10 further includes an accelerometer or other physiologic sensor 908, commonly referred to as a "rate-responsive" sensor because it is typically used to adjust pacing stimulation rate according to the exercise state of the patient. However, the physiological sensor 908 may further be used to detect changes in cardiac output, changes in the physiological condition of the heart, or diurnal changes in activity (e.g., detecting sleep and wake states) and to detect arousal from sleep. Accordingly, the microcontroller 860 responds by adjusting the various pacing parameters (such as rate, AV Delay, V-V Delay, etc.) at which the atrial and ventricular pulse generators, 870 and 872, generate stimulation pulses. While shown as being included within pacer/ICD 10, it is to be understood that the physiologic sensor 908 may also be external to pacer/ICD 10, yet still be implanted within or carried by the patient. A common type of rate responsive sensor is an activity sensor incorporating an accelerometer or a piezoelectric crystal, which is mounted within the housing 840 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 910, which provides operating power to all of the circuits shown in FIG. 14. The battery 910 may vary depending on the capabilities of pacer/ICD 10. If the system only provides low voltage therapy, a lithium iodine or lithium copper fluoride cell may be utilized. For pacer/ICD 10, which employs shocking therapy, the battery 910 must be capable of operating at low current drains for long periods, and then be capable of providing high-current pulses (for capacitor charging) when the patient requires a shock pulse. The battery 910 must also have a predictable discharge characteristic so that elective replacement time can be detected. Accordingly, pacer/ICD 10 is preferably capable of high voltage therapy and appropriate batteries.

As further shown in FIG. 14, pacer/ICD 10 is shown as having an impedance measuring circuit 912 which is enabled by the microcontroller 860 via a control signal 914. Various uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, measuring lead resistance, etc. The impedance measuring circuit 120 is advantageously coupled to the switch 94 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 860 further controls a shocking circuit 916 by way of a control signal 918. The shocking circuit 916 generates shocking pulses of low (up to 0.5 joules), moderate (0.5-11 joules) or high energy (11 to at least 40 joules), as controlled by the microcontroller 860. Such shocking pulses are applied to the heart of the patient through at least two shocking electrodes, and as shown in this embodiment, selected from the left atrial coil electrode 828, the RV coil electrode 836, and/or the SVC coil electrode 838. The housing 840 may act as an active electrode in combination with the RV electrode 836, or as part of a split electrical vector using the SVC coil electrode 838 or the left atrial coil electrode 828 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules), delivered asynchronously (since R-waves may be too disorganized), and pertaining exclusively to the treatment of fibrillation. Accordingly, the microcontroller 860 is capable of controlling the synchronous or asynchronous delivery of the shocking pulses.

Alternative Lead Implementation with Quarter Wavelength Spacing

Figure 17:
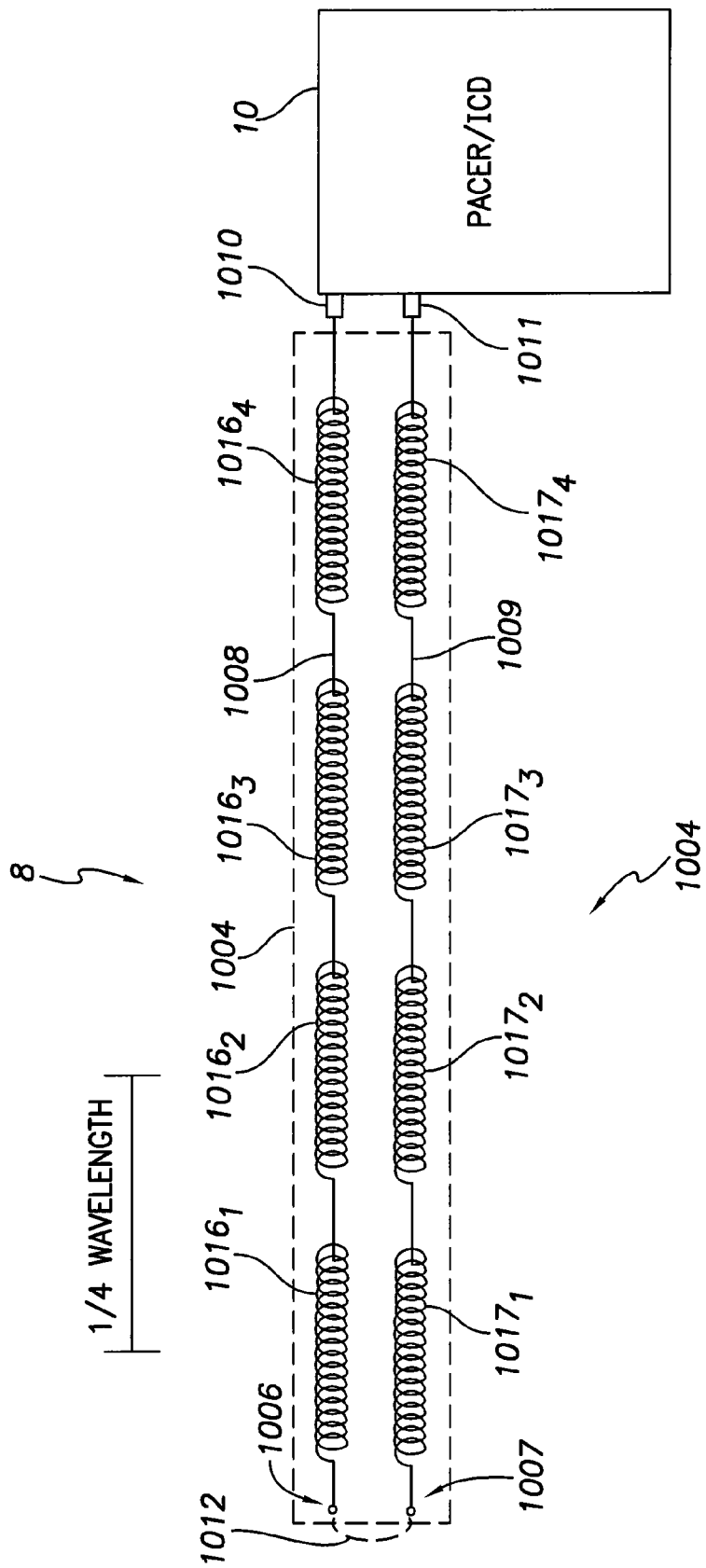
FIG. 17 is a block diagram, partly in schematic form, illustrating an alternative bipolar embodiment for use as one of the leads of FIG. 1, wherein insulated coils are formed at both proximal and distal ends of the conductors of the lead and at ¼ wavelength locations therebetween, and also illustrating a pacer/ICD connected to the lead.

FIG. 17 illustrates another bipolar example of one of the leads of FIG. I (shown schematically without any coiling or wrapping of the proximal end of the lead around the device as in FIG. 1.) The implementation of FIG. 17 is similar to that of FIG. 2, but conducting coils are provided at both distal and proximal ends of the lead and at quarter wavelength locations therebetween. Only pertinent differences between the embodiment of FIG. 17 and that of FIG. 2 will be described in detail.

Briefly, the figure shows an implantable system having a pacer/ICD 1010 with a bipolar lead 1004. The bipolar lead includes a tip electrode 1006 connected to the pacer/ICD via a tip conductor 1008 coupled to a tip connector 1010 of the pacer/ICD. Tip conductor 1008 includes, near its distal end, an insulated coil portion $1016_1$ formed as an inductive bandstop filter for filtering RF signals associated with MRIs. Conductor 1008 also includes, near its proximal end, an insulated coil portion $1016_4$ also formed as an inductive bandstop filter. Additionally, intermediate insulated coils $1016_2$ and $1016_3$ are provided, with the various coils spaced at quarter wavelength locations along the lead. That is, each coil is preferred to be distributed at about ¼ wavelength locations along the lead (based on the wavelengths of current flowing in lead conductors in the presence of MRI RF fields or other strong magnetic fields.)

For an MRI, the wavelengths of RF current induced in the leads varies typically about the length of the lead or are integer multiples or fractions thereof, which depends on, e.g., lead structure, lead length and MRI RF frequencies. If the wavelength of the induced currents is expected to be about equal to the length of the lead, then four coils are provided (as shown). The coils need not be positioned at exactly quarter wavelengths. Also, depending upon the length of the lead and the relevant wavelength, more or fewer coils might be provided along the lead.

The bipolar lead also includes a ring electrode 1007 electrically connected to the pacer/ICD via a ring conductor 1009 coupled to a ring connector 1011 of the pacer/ICD. Ring conductor 1009 includes, near its distal end, an insulated coil portion $1017_1$ formed as an inductive bandstop filter for filtering RF signals associated with MRIs. Conductor 1009 also includes, near its proximal end, an insulated coil portion $1017_4$ also formed as an inductive bandstop filter. Additionally, intermediate insulated coils $1017_2$ and $1017_3$ are provided, with the various coils again spaced at quarter wavelength locations along the lead.

Note that, in FIG. 17 as in FIG. 2, the tip and ring conductors are shown schematically as being side-by-side. Depending upon the actual implementation, the tip conductor might be positioned inside the ring conductor (as with a coaxial lead) or might be physically positioned side-by-side (as with a co-radial lead.) The size, shapes and electrical parameters of the coil portions of the lead conductors can be configured so as to collectively impede the conduction of signals at selected RF frequencies, such as at about 64 MHz or at about 128 MHz. Preferably, the insulated coil portions of the conductors are configured to provide high impedance (preferably 1000 ohms or more) at one or more selected RF signal frequencies.

What have been described are systems and methods for use with a set of pacing/sensing leads for use with a pacer/ICD. Principles of the invention may be exploiting using other implantable systems or in accordance with other techniques. Thus, while the invention has been described with reference to particular exemplary embodiments, modifications can be made thereto without departing from the scope of the invention.

What is claimed is:

1. A lead for use with an implantable medical device for implant within a patient, the lead comprising:

a tip electrode and a tip conductor coupled to the tip electrode;

an electrode for placement adjacent patient tissues; and a conductor operative to route signals along the lead between the electrode and the implantable medical device, with a portion of the conductor formed as an insulated coil that is configured to be capacitively coupled to the tip conductor to provide inductive-capacitive bandstop filtering of radio-frequency (RF) signals.

2. The lead of claim 1 wherein the portion formed as an insulated coil is configured to achieve bandstop filtering at one or more of about 64 MHz and about 128 MHz.

3. The lead of claim 1 wherein the portion formed as an insulated coil is configured to provide sufficient impedance at radio frequencies to substantially reduce heating of the lead during magnetic resonance imaging (MRI).

4. The lead of claim 3 wherein the portion formed as an insulated coil provides at least 1000 ohms of impedance at the RF signal frequencies of MRI fields.

5. The lead of claim 1 wherein the portion formed as an insulated coil is positioned along a distal end of the lead.

6. The lead of claim 1 wherein the portion formed as an insulated coil includes portions positioned along a distal end of the lead and a proximal end of the lead.

7. The lead of claim 1 wherein the portion formed as an insulated coil includes portions positioned at about ¼ wavelength locations along the lead.

8. The lead of claim 1 wherein the lead is coaxial.

9. The lead of claim 8 wherein at least a portion of a tip conductor of the lead is formed as an insulated coil and configured to provide inductive bandstop filtering of RF signals.

10. The lead of claim 8 wherein at least a portion of the conductor is formed as an insulated coil and configured to provide inductive bandstop filtering of RF signals.

11. The lead of claim 10 wherein the portion of the ring conductor formed as an insulated coil covers a portion of the tip conductor formed as an insulated coil to provide a pair of nested coils.

12. The lead of claim 8 wherein capacitive coupling is provided between a ring electrode and a tip conductor of the lead at RF.

13. The lead of claim 12 wherein the ring electrode is configured to have an inner diameter just larger than an outer diameter of the tip conductor so as to provide capacitive shunting between the ring electrode and the tip conductor at RF.

14. The lead of claim 13 wherein the ring electrode is configured to have a relatively long length relative to its diameter to enhance the capacitive shunting between the ring electrode and the tip conductor at RF.

15. The lead of claim 11 wherein a capacitive transition is provided between the portion of the ring conductor formed as an insulated coil and other portions of the ring conductor.

16. The lead of claim 15 wherein the capacitive transition is configured to provide capacitive shunting between the tip and ring conductors at RF.

17. The lead of claim 15 wherein a conducting polymer is provided along the portion of capacitive transition to enhance shunting.

18. The lead of claim 15 wherein a conducting polymer tubing is provided between the ring electrode and adjacent portions of the insulated coil of the tip conductor inside the ring electrode.

19. The lead of claim 18 wherein a conducting polymer core is provided within the insulated coil of the tip conductor inside the ring electrode.

20. The lead of claim 15 wherein a capacitive transition is provided between the portion of the ring conductor formed as an insulated coil and other portions of the ring conductor and wherein a conducting polymer tubing is provided between the capacitive transition and adjacent portions of the insulated coil of the tip conductor inside the capacitive transition.

21. The lead of claim 20 wherein a conducting polymer core is provided within the insulated coil of the tip conductor inside the capacitive transition.

22. The lead of claim 17 wherein the conducting polymer is configured to function as an RF shunt.

23. The lead of claim 15 wherein an insulation layer of high dielectric material is provided between the ring electrode and adjacent portions of the insulated coil of the tip conductor inside the ring electrode.

24. The lead of claim 11 wherein at least two portions of the tip and ring conductors are formed as nested insulated coil inductors.

25. The lead of claim 24 wherein a conducting polymer is provided between the at least two portions.

26. The lead of claim 24 wherein the at least two portions are configured to provide different self-resonance frequencies (SRFs).

27. The lead of claim 1 wherein the portion formed as an insulated coil is configured with about 400 turns.

28. The lead of claim 1 further including conductive shielding formed along at least a portion of the lead.

29. The lead of claim 28 wherein the conductive shielding is mounted to an outer sleeve.

30. The lead of claim 28 wherein the conductive shielding is embedded within a sleeve insulation layer.

31. A bipolar lead for use with an implantable medical device for implant within a patient, the lead comprising:
   first and second electrodes for placement adjacent patient tissues;
   a first conductor operative to route signals along the lead between the first electrode and the implantable medical device;
   a second conductor operative to route signals along the lead between the second electrode and the implantable medical device;
   wherein portions of the tip and ring conductors are formed as insulated coils that are configured to be capacitively coupled to each other to provide inductive-capacitive bandstop filtering of radio-frequency (RF) signals.

32. An implantable medical system for implant within a patient comprising:
   an implantable cardiac rhythm management device; and
   a lead for use with the implantable medical device wherein the lead includes an electrode for placement adjacent patient tissues and a conductor operative to route signals along the lead between the electrode and the implantable medical device and further comprises a tip electrode and a tip conductor coupled to the tip electrode, with a portion of the conductor formed as an insulated coil that is configured to be capacitively coupled to the tip conductor to provide inductive-capacitive bandstop filtering of radio-frequency (RF) signals.

* * * * *